(12) United States Patent
Bruno et al.

(10) Patent No.: US 8,981,086 B2
(45) Date of Patent: Mar. 17, 2015

(54) PHOSPHINE-LIGATED PALLADIUM SULFONATE PALLADACYCLES

(71) Applicant: Massachusetts Institute of Technology, Cambridge, MA (US)

(72) Inventors: Nicholas C. Bruno, California, MD (US); Stephen L. Buchwald, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/521,727

(22) Filed: Oct. 23, 2014

(65) Prior Publication Data

US 2015/0045570 A1 Feb. 12, 2015

Related U.S. Application Data

(62) Division of application No. 13/799,620, filed on Mar. 13, 2013, now Pat. No. 8,889,857.

(60) Provisional application No. 61/657,377, filed on Jun. 8, 2012.

(51) Int. Cl.
*C07F 15/00* (2006.01)
*C07F 9/28* (2006.01)

(52) U.S. Cl.
CPC .................................. *C07F 15/006* (2013.01)
USPC ............... 544/64; 556/137; 556/136; 556/28; 549/212; 549/206; 548/101; 548/402; 546/2

(58) Field of Classification Search
USPC ......... 556/28, 136, 137; 546/2; 548/101, 402; 544/64; 549/206, 212
See application file for complete search history.

(56) References Cited

U.S. PATENT DOCUMENTS

2008/0064892 A1   3/2008   Preston et al.

OTHER PUBLICATIONS

Briscoe et al., "A New Class of Easily Activated Palladium Precatalysts for Facile C—N Cross-Coupling Reactions and the Low Temperature Oxidative Addition of Aryl Chlorides," J. Am. Chem. Soc., 130:6686-6687 (2008).
Favier et al., "Kinetico-mechanistic studies of C—H bond activation on new Pd complexes containing N,N'—chelating ligands," Dalton Trans., pp. 123-132 (2005).
Kinzel et al., "A New Palladium Precatalyst Allows for the Fast Suzuki-Miyaura Coupling Reactions of Unstable Polyfluorophenyl and 2-Heteroaryl Boronic Acids," JACS, 132:14073-14075 (2010).
Verrier et al., "Recent advances in direct C—H arylation: Methodology, selectivity and mechanism in oxazole series," Beilstein Journal of Organic Chemistry, 7:1584-1601 (2011).
International Search Report dated May 21, 2013 from PCT/US2013/030779.

*Primary Examiner* — Kristin Vajda
(74) *Attorney, Agent, or Firm* — Foley Hoag LLP

(57) ABSTRACT

Described are palladium precatalysts, and methods of making and using them. The palladium precatalysts show improved stability and improved reactivity in comparison to previously-described palladium precatalysts.

12 Claims, 14 Drawing Sheets

| Ligand | Precatalyst Yield (%) | Ligand | Precatalyst Yield (%) |
|---|---|---|---|
| tBuXPhos | 91% | BrettPhos | 92% |
| SPhos | 93% | RuPhos | 91% |
| DavePhos | 97% | tBuDavePhos | 97% |
| XantPhos | 87% | PPh₃ | 89% |
| P(o-tol)₃ | 82% | PCy₃ | 95% |
| P(tBu)₃ | 87% | BINAP | 93% |
| dppf | 89% | dppp | 91% |

R = alkyl, aryl

*DinoPhos*

PHOSPHINE-LIGATED PALLADIUM SULFONATE PALLADACYCLES

RELATED APPLICATIONS

This application is a divisional of U.S. patent application Ser. No. 13/799,620, filed Mar. 13, 2013; which claims the benefit of priority to U.S. Provisional Patent Application Ser. No. 61/657,377, filed Jun. 8, 2012.

STATEMENT REGARDING FEDERALLY SPONSORED RESEARCH OR DEVELOPMENT

This invention was made with Government support under Grant Nos. GM046059 and GM058160 awarded by the National Institutes of Health. The government has certain rights in this invention.

BACKGROUND OF THE INVENTION

Transition metal catalyst complexes play important roles in many areas of chemistry. Catalyst complexes are recognized to be influenced by the characteristics of the transition metal and those of the associated ligands. For example, structural features of the ligands can influence reaction rate, regioselectivity, and stereoselectivity in reactions involving the catalyst complexes. For example, in coupling reactions, electron-withdrawing ligands can be expected to slow oxidative addition to, and speed reductive elimination from, the metal center; and, conversely, electron-rich ligands can be expected to speed oxidative addition to, and slow reductive elimination from, the metal center.

Although phosphine-ligated Pd(0) complexes constitute the active catalyst in many reactions, such complexes are usually difficult to prepare and extremely air-sensitive. Tris(dibenzylideneacetone)dipalladium(0) ($Pd_2(dba)_3$), which was developed to serve as a stable source of Pd(0), includes coordinating dibenzylideneacetone ligands that can significantly retard the formation of the actual active catalyst complex and/or diminish its ultimate reactivity. The use of a Pd(II) salt, such as $Pd(OAc)_2$, which circumvents problems of precatalyst instability, requires in situ reduction in order to generate the active Pd(0) complex. In light of the complications in forming phosphine-ligated Pd(0) complexes, precatalyst scaffolds constituting the source of Pd and phosphine ligand were developed. See FIG. 1. These precatalysts formed the active, monoligated Pd complex under mild conditions and without the need for exogenous additives.

However, working with known precatalysts can be problematic. For example, the three-step preparation of precatalyst 1 (FIG. 1) involves the handling of sensitive organometallic intermediates and is not amenable to large-scale production. Additionally, precatalyst 1 is prone to decomposition in solution after a few hours and is not compatible with bulkier ligands, such as tBuBrettPhos, RockPhos, AdBrettPhos, and Me₄tBuXPhos. See FIG. 10. Precatalyst 2, which can be prepared relatively simply, is not widely suitable; for example, it cannot be formed with bulkier ligands, such as BrettPhos, tBuXPhos, tBuBrettPhos, RockPhos, AdBrettPhos, and Me₄tBuXPhos; additionally, it does not exhibit prolonged stability in solution.

There exists a need for a new class of air-stable, moisture-stable, solution-stable, one-component Pd precatalysts that may be activated under standard reaction conditions and ensures the formation of the active complex, $L_1Pd(0)$, with a wide range of ligands.

SUMMARY OF THE INVENTION

In certain embodiments, the invention relates to a precatalyst of formula I

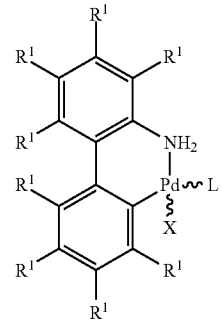

I wherein, independently for each occurrence,
X is a non-coordinating anion;
$R^1$ is H, alkyl, haloalkyl, hydroxy, alkoxy, aryloxy, aryl, or halo; and
L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula II

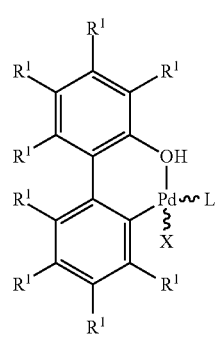

II wherein, independently for each occurrence,
X is a non-coordinating anion;
$R^1$ is H, alkyl, haloalkyl, hydroxy, alkoxy, aryloxy, aryl, or halo; and
L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula III

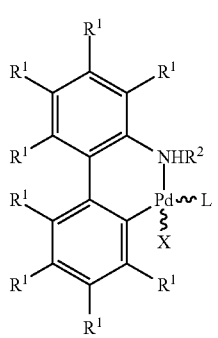

III wherein, independently for each occurrence,
X is a non-coordinating anion;
$R^1$ is H, alkyl, haloalkyl, hydroxy, alkoxy, aryloxy, aryl, or halo;

L is a trialkylphosphine, triarylphosphine, dialkylarylphosphine, alkyldiarylphosphine, bis(phosphine), phosphoramide, amine, bis(amine), or N-heterocyclic carbene; and $R^2$ is alkyl, haloalkyl or aryl.

In certain embodiments, the invention relates to a precatalyst of formula VII

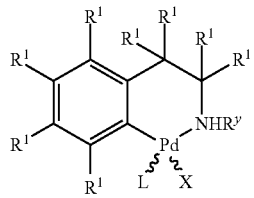

VII wherein, independently for each occurrence,

X is a non-coordinating anion;

$R^1$ is H, alkyl, haloalkyl, hydroxy, alkoxy, aryloxy, aryl, or halo;

L is a trialkylphosphine, triarylphosphine, dialkylarylphosphine, alkyldiarylphosphine, bis(phosphine), phosphoramide, amine, bis(amine), or N-heterocyclic carbene; and $R^y$ is H, alkyl, haloalkyl or aryl.

In certain embodiments, the invention relates to any one of the aforementioned precatalysts, wherein X is selected from the group consisting of boron tetrafluoride, tetraarylborates (such as $B(C_6F_5)_4^-$ and $(B[3,5-(CF_3)_2C_6H_3]_4)^-$), hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

In certain embodiments, the invention relates to a dimer of formula IX

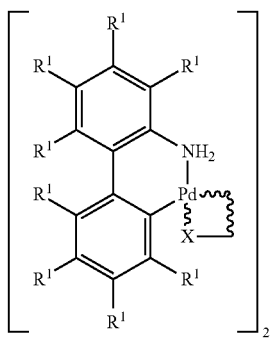

IX wherein, independently for each occurrence,

X is a non-coordinating anion; and $R^1$ is H, alkyl, haloalkyl, hydroxy, alkoxy, aryloxy, aryl, or halo.

In certain embodiments, the invention relates to a dimer of formula X

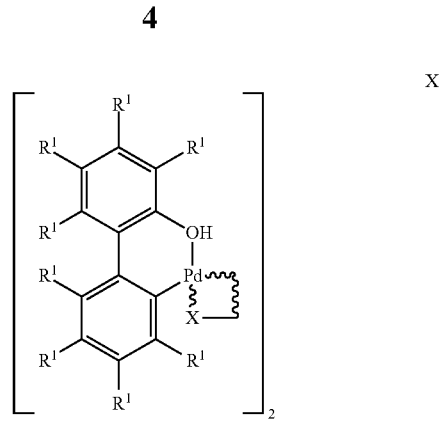

X wherein, independently for each occurrence,

X is a non-coordinating anion; and $R^1$ is H, alkyl, haloalkyl, hydroxy, alkoxy, aryloxy, aryl, or halo.

In certain embodiments, the invention relates to a dimer of formula XI

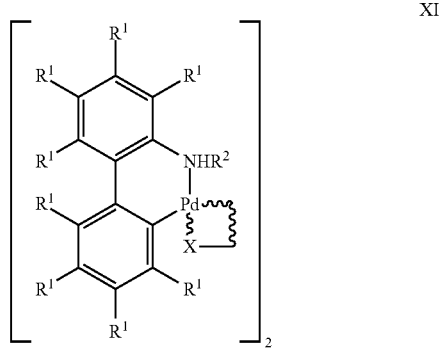

XI wherein, independently for each occurrence,

X is a non-coordinating anion; and $R^1$ is H, alkyl, haloalkyl, hydroxy, alkoxy, aryloxy, aryl, or halo; and $R^2$ is alkyl, haloalkyl or aryl.

In certain embodiments, the invention relates to a dimer of formula XV

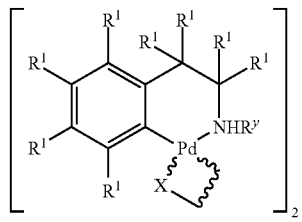

XV wherein, independently for each occurrence,

X is a non-coordinating anion; and $R^1$ is H, alkyl, haloalkyl, hydroxy, alkoxy, aryloxy, aryl, or halo; and $R^y$ is H, alkyl, haloalkyl or aryl.

In certain embodiments, the invention relates to any one of the aforementioned dimers, wherein X is selected from the group consisting of boron tetrafluoride, tetraarylborates (such as $B(C_6F_5)_4^-$ and $(B[3,5-(CF_3)_2C_6H_3]_4)^-$), hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

DETAILED DESCRIPTION OF THE INVENTION

Overview

Figure 1:
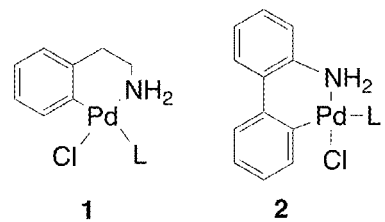
FIG. 1 depicts two known precatalysts. The stereochemistry at Pd in the precatalysts is cis or trans.

In certain embodiments, the invention relates to a palladium sulfonate precatalyst. In certain embodiments, the synthesis of the precatalysts may be easily accomplished from commercially available starting materials. In certain embodiments, the precatalysts incorporate any of a wide range of phosphine ligands. In certain embodiments, the precatalysts are markedly stable in solution. In certain embodiments, the precatalysts are stable in solution for greater than about one month.

Precatalysts of the Invention

In certain embodiments, the invention relates to a precatalyst of formula I

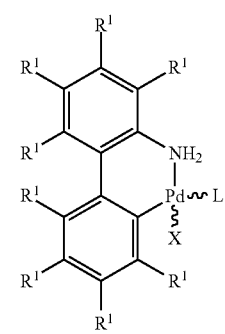

wherein, independently for each occurrence,

X is a non-coordinating anion;

$R^1$ is H, alkyl, haloalkyl, hydroxy, alkoxy, aryloxy, aryl, or halo; and

L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula II

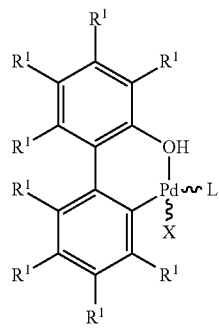

II wherein, independently for each occurrence,
X is a non-coordinating anion;
$R^1$ is H, alkyl, haloalkyl, hydroxy, alkoxy, aryloxy, aryl, or halo; and
L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula III

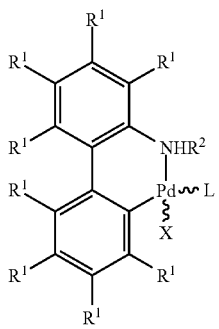

III wherein, independently for each occurrence,
X is a non-coordinating anion;
$R^1$ is H, alkyl, haloalkyl, hydroxy, alkoxy, aryloxy, aryl, or halo;
L is a trialkylphosphine, triarylphosphine, dialkylarylphosphine, alkyldiarylphosphine, bis(phosphine), phosphoramide, amine, bis(amine), or N-heterocyclic carbene; and
$R^2$ is alkyl, haloalkyl or aryl.

In certain embodiments, the invention relates to a precatalyst of formula IV

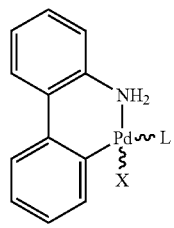

IV wherein, independently for each occurrence,
X is a non-coordinating anion; and
L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula V

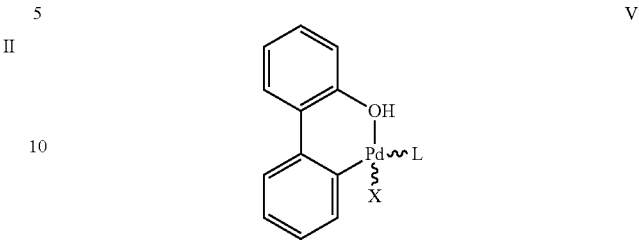

V wherein, independently for each occurrence,
X is a non-coordinating anion; and
L is a trialkylphosphine, triarylphosphine, dialkylarylphosphine, alkyldiarylphosphine, bis(phosphine), phosphoramide, amine, bis(amine), or N-heterocyclic carbene.

In certain embodiments, the invention relates to a precatalyst of formula VI

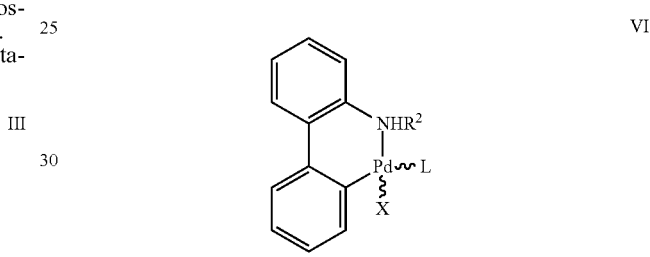

VI wherein, independently for each occurrence,
X is a non-coordinating anion;
L is a trialkylphosphine, triarylphosphine, dialkylarylphosphine, alkyldiarylphosphine, bis(phosphine), phosphoramide, amine, bis(amine), or N-heterocyclic carbene; and
$R^2$ is alkyl, haloalkyl or aryl.

In certain embodiments, the invention relates to a precatalyst of formula VII

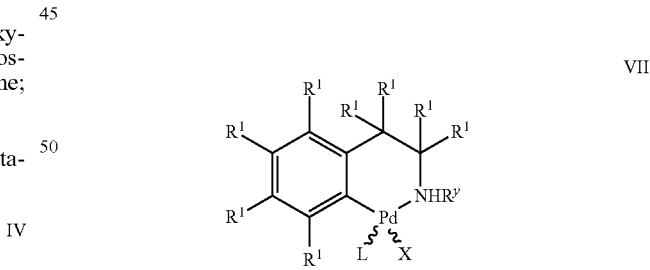

VII wherein, independently for each occurrence,
X is a non-coordinating anion;
$R^1$ is H, alkyl, haloalkyl, hydroxy, alkoxy, aryloxy, aryl, or halo;
L is a trialkylphosphine, triarylphosphine, dialkylarylphosphine, alkyldiarylphosphine, bis(phosphine), phosphoramide, amine, bis(amine), or N-heterocyclic carbene; and
$R^y$ is H, alkyl, haloalkyl or aryl.

In certain embodiments, the invention relates to a precatalyst of formula VIII

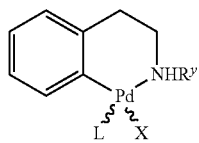
VIII wherein, independently for each occurrence,

X is a non-coordinating anion;

L is a trialkylphosphine, triarylphosphine, dialkylarylphosphine, alkyldiarylphosphine, bis(phosphine), phosphoramide, amine, bis(amine), or N-heterocyclic carbene; and $R^y$ is H, alkyl, haloalkyl or aryl.

In certain embodiments, the invention relates to a precatalyst of any one of formulae I, II, III, IV, V, VI, VII, or VIII, wherein L is a ligand described in U.S. Pat. No. 7,858,784, which is hereby incorporated by reference in its entirety.

In certain embodiments, the invention relates to a precatalyst of any one of formulae I, II, III, IV, V, VI, VII, or VIII, wherein L is a ligand described in U.S. Patent Application Publication No. 2011/0015401, which is hereby incorporated by reference in its entirety.

In certain embodiments, the invention relates to a precatalyst of any one of formulae I, II, III, IV, V, VI, VII, or VIII, wherein L is selected from the group consisting of

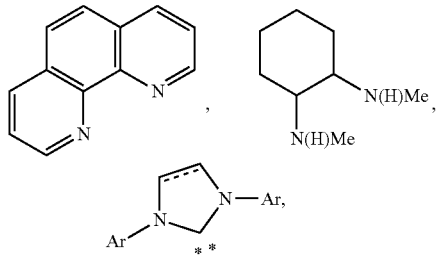

and tetramethylethylenediamine (TMEDA).

In certain embodiments, the invention relates to a precatalyst of any one of formulae I, II, III, IV, V, VI, VII, or VIII, wherein L is

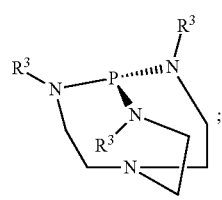

and $R^3$ is H or alkyl.

In certain embodiments, the invention relates to any one of the aforementioned precatalysts, wherein L is selected from the group consisting of $PPh_3$, $Ph_2P-CH_3$, $PhP(CH_3)_2$, $P(o-tol)_3$, $PCy_3$, $P(tBu)_3$, BINAP, dppb, dppe, dppf, dppp,

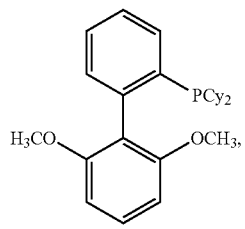
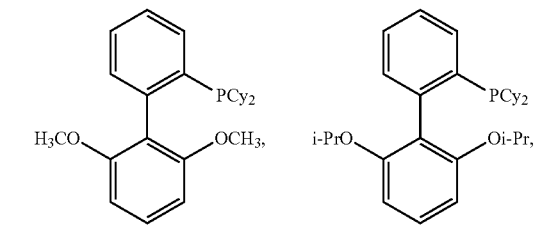
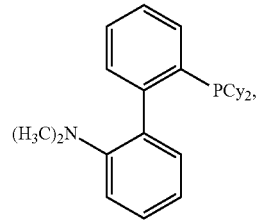
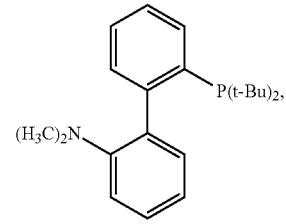
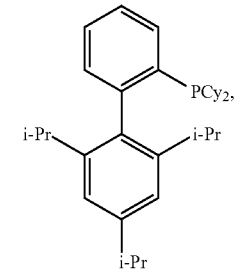
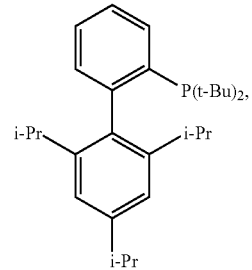
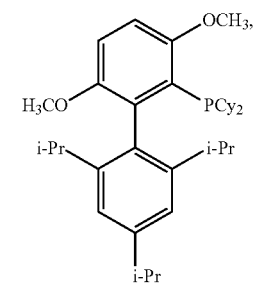
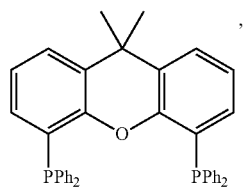
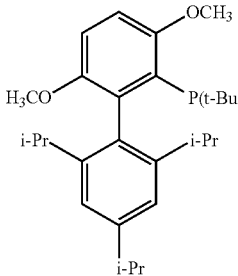
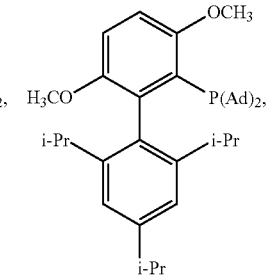
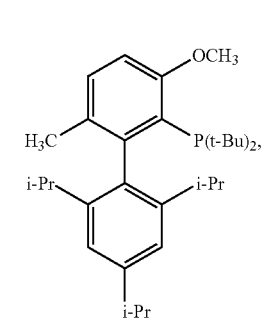
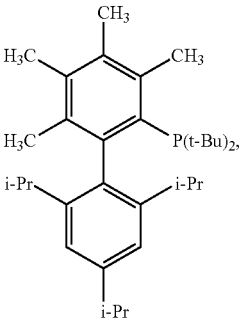

-continued
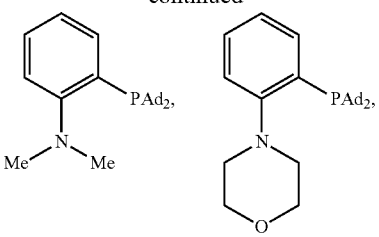
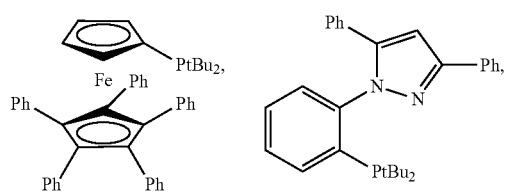
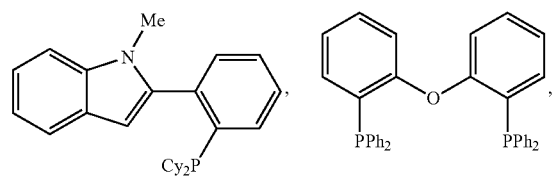
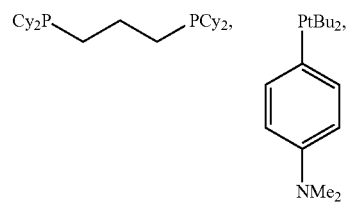
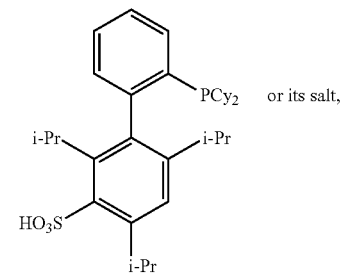
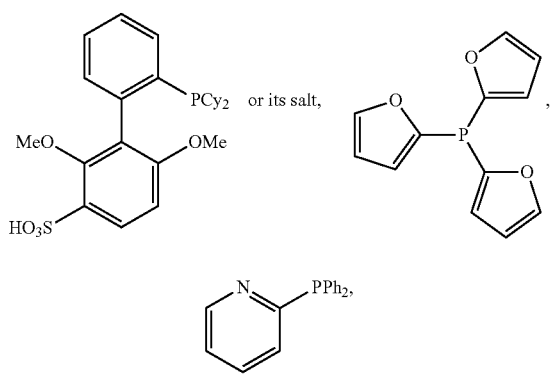
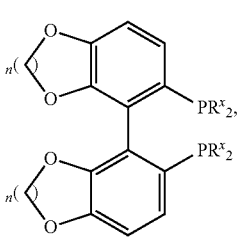
-continued
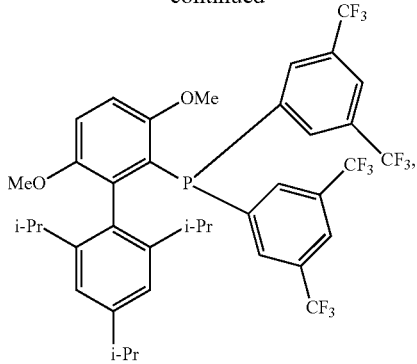
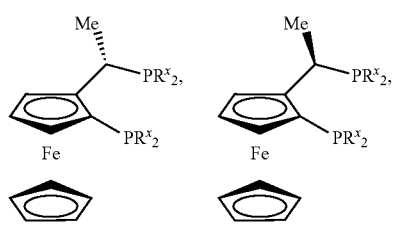
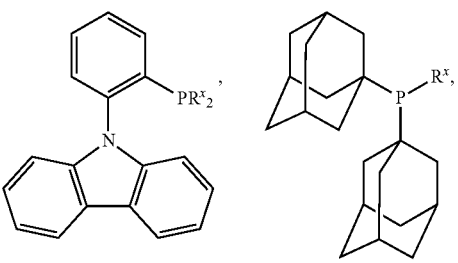
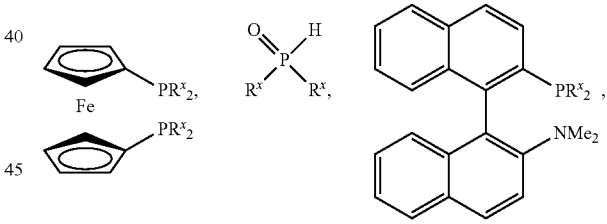
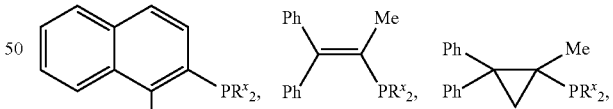
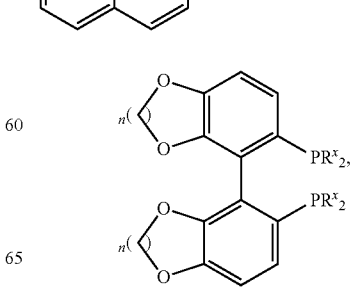

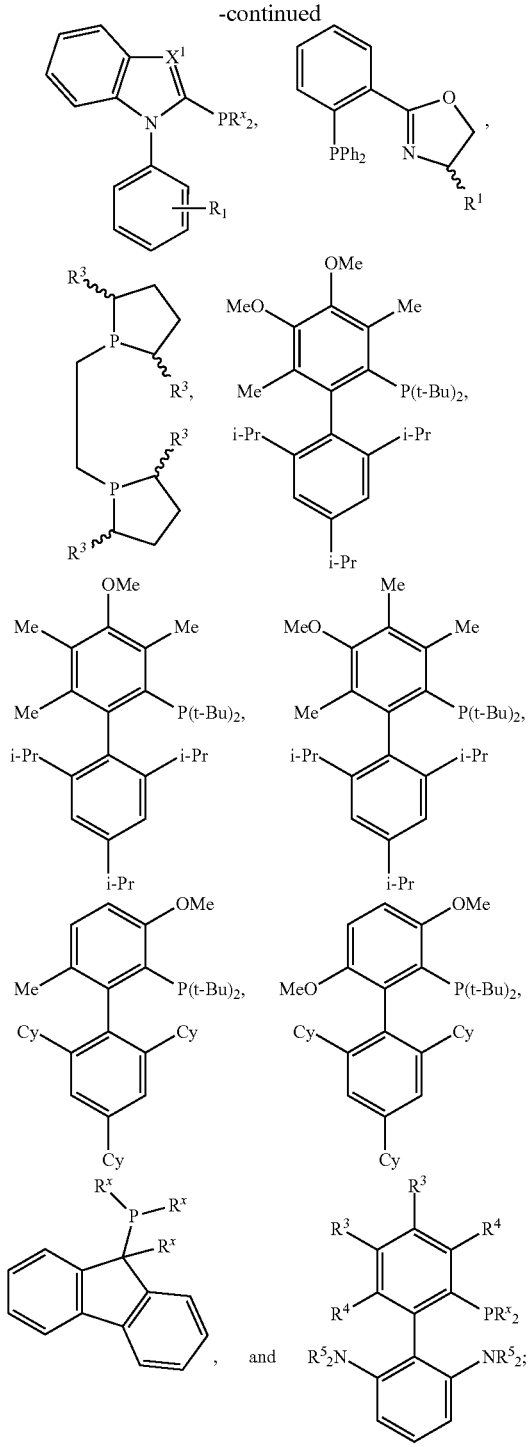

$R^x$ is alkyl, aralkyl, cycloalkyl, or aryl;
$X^1$ is CH or N;
$R^3$ is H or alkyl;
$R^4$ is H, alkoxy, or alkyl;
$R^5$ is alkyl or aryl; and
n is 1, 2, 3, or 4.

In certain embodiments, the invention relates to any one of the aforementioned precatalysts, wherein X is selected from the group consisting of boron tetrafluoride, tetraarylborates (such as $B(C_6F_5)_4^-$ and $(B[3,5\text{-}(CF_3)_2C_6H_3]_4)^-$), hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

In certain embodiments, the invention relates to any one of the aforementioned precatalysts, wherein X is alkylsulfonate; and the alkyl is substituted alkyl. In certain embodiments, the invention relates to any one of the aforementioned precatalysts, wherein X is alkylsulfonate; and the alkyl is unsubstituted alkyl.

In certain embodiments, the invention relates to any one of the aforementioned precatalysts, wherein X is alkylsulfonate; and the alkyl is methyl, ethyl, propyl, or butyl. In certain embodiments, the invention relates to any one of the aforementioned precatalysts, wherein X is alkylsulfonate; and the alkyl is methyl or ethyl.

In certain embodiments, the invention relates to any one of the aforementioned precatalysts, wherein X is haloalkylsulfonate. In certain embodiments, the invention relates to any one of the aforementioned precatalysts, wherein X is fluoroalkylsulfonate.

In certain embodiments, the invention relates to any one of the aforementioned precatalysts, wherein X is fluoromethylsulfonate. In certain embodiments, the invention relates to any one of the aforementioned precatalysts, wherein X is trifluoromethylsulfonate.

In certain embodiments, the invention relates to any one of the aforementioned precatalysts, wherein X is cycloalkylalkylsulfonate. In certain embodiments, the invention relates to any one of the aforementioned precatalysts, wherein X is

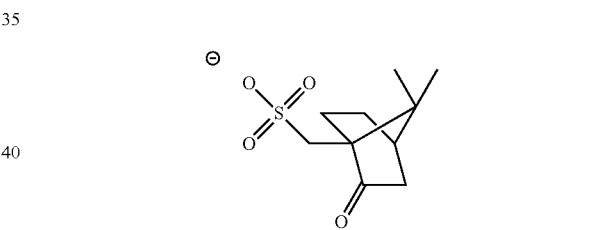

or its enantiomer.

In certain embodiments, the invention relates to any one of the aforementioned precatalysts, wherein X is arylsulfonate; and the aryl is substituted aryl. In certain embodiments, the invention relates to any one of the aforementioned precatalysts, wherein X is arylsulfonate; and the aryl is unsubstituted aryl.

In certain embodiments, the invention relates to any one of the aforementioned precatalysts, wherein X is phenylsulfonate. In certain embodiments, the invention relates to any one of the aforementioned precatalysts, wherein X is methylphenylsulfonate. In certain embodiments, the invention relates to any one of the aforementioned precatalysts, wherein X is p-toluenesulfonate.

In certain embodiments, the invention relates to any one of the aforementioned precatalysts, wherein $R^1$ is H or alkyl. In certain embodiments, the invention relates to any one of the aforementioned precatalysts, wherein $R^1$ is H.

In certain embodiments, the invention relates to any one of the aforementioned precatalysts, wherein $R^2$ is substituted alkyl. In certain embodiments, the invention relates to any one of the aforementioned precatalysts, wherein $R^2$ is unsubstituted alkyl.

In certain embodiments, the invention relates to any one of the aforementioned precatalysts, wherein $R^2$ is methyl, ethyl, propyl, or butyl.

In certain embodiments, the invention relates to any one of the aforementioned precatalysts, wherein $R^2$ is substituted aryl. In certain embodiments, the invention relates to any one of the aforementioned precatalysts, wherein $R^2$ is unsubstituted aryl.

In certain embodiments, the invention relates to any one of the aforementioned precatalysts, wherein $R^2$ is phenyl.

In certain embodiments, the invention relates to a compound selected from the group consisting of:

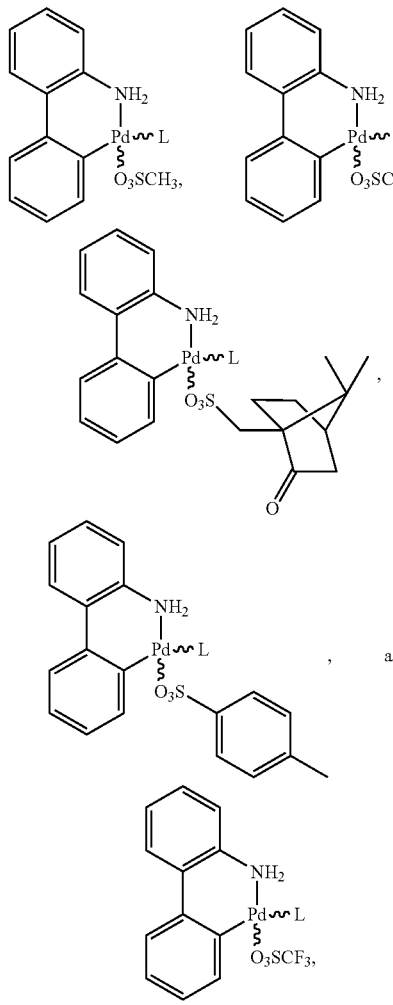

wherein L is selected from the group consisting of PPh$_3$, P(o-tol)$_3$, PCy$_3$, P(tBu)$_3$, BINAP, dppf, dppp,

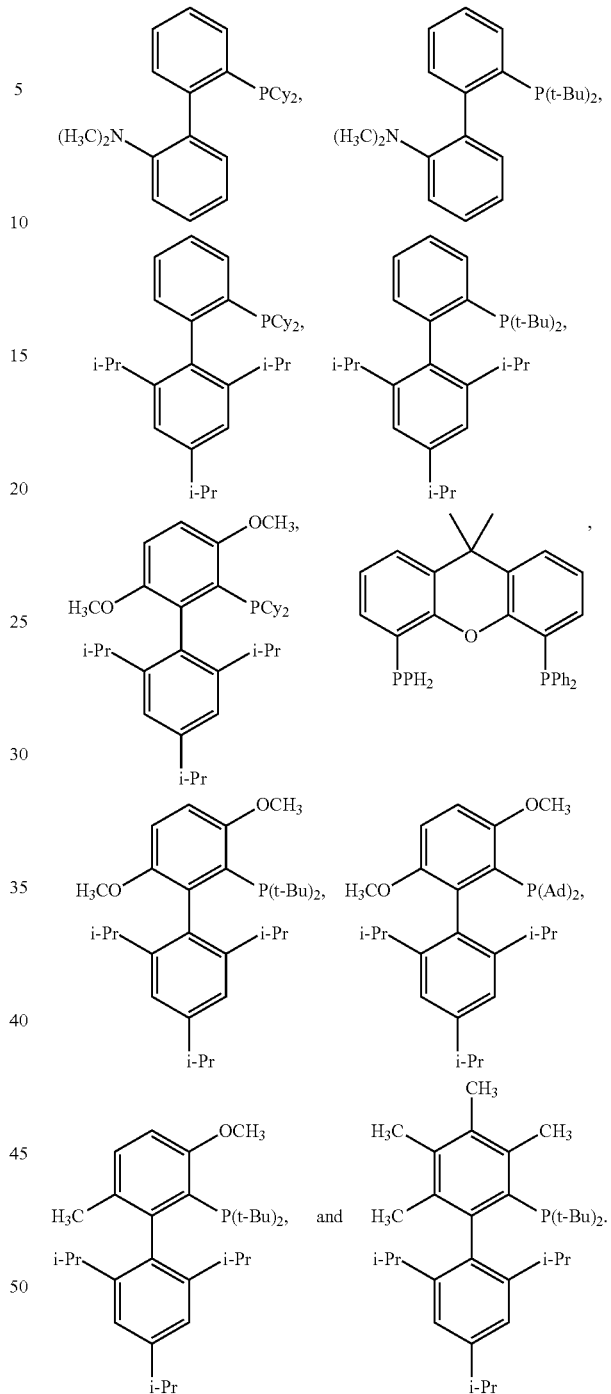

In certain embodiments, the invention relates to a compound of the following structure:

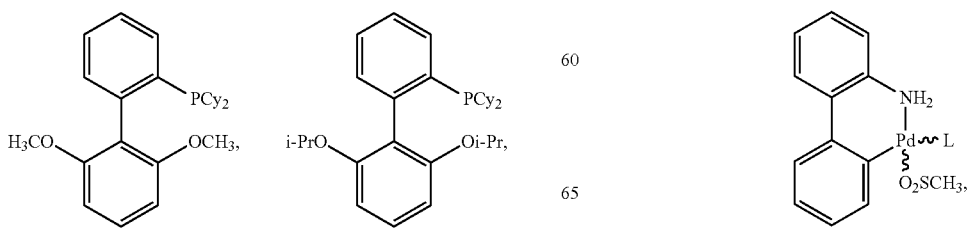

wherein L is selected from the group consisting of PPh₃, P(o-tol)₃, PCy₃, P(tBu)₃, BINAP, dppf,
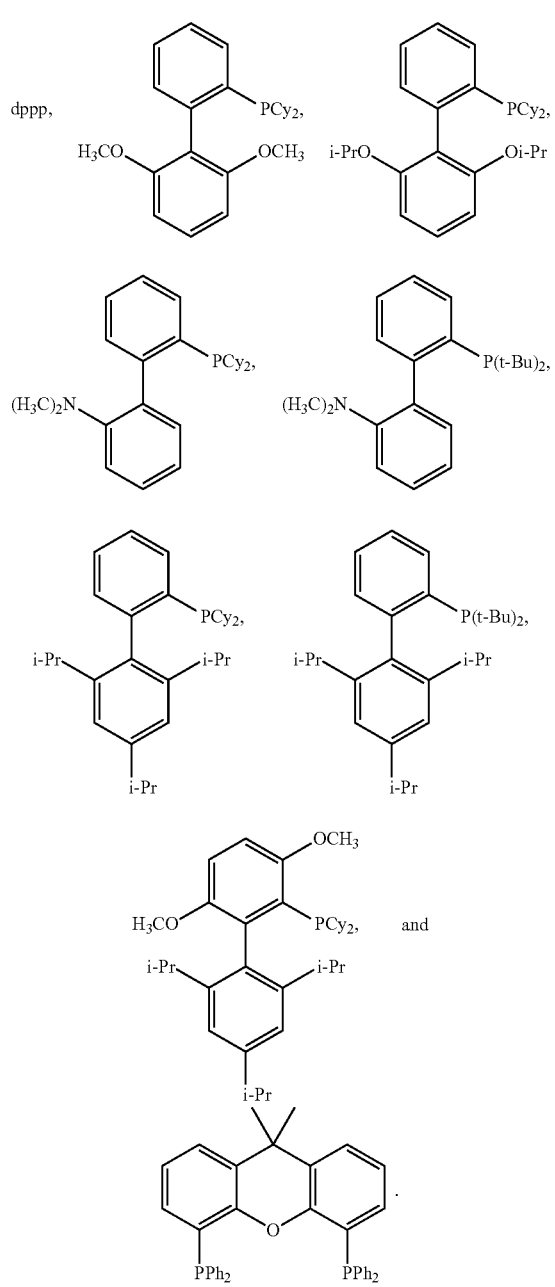
In certain embodiments, the invention relates to a compound of the following structure:
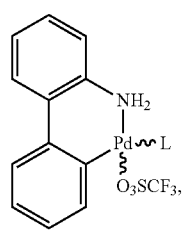
wherein L is selected from the group consisting of
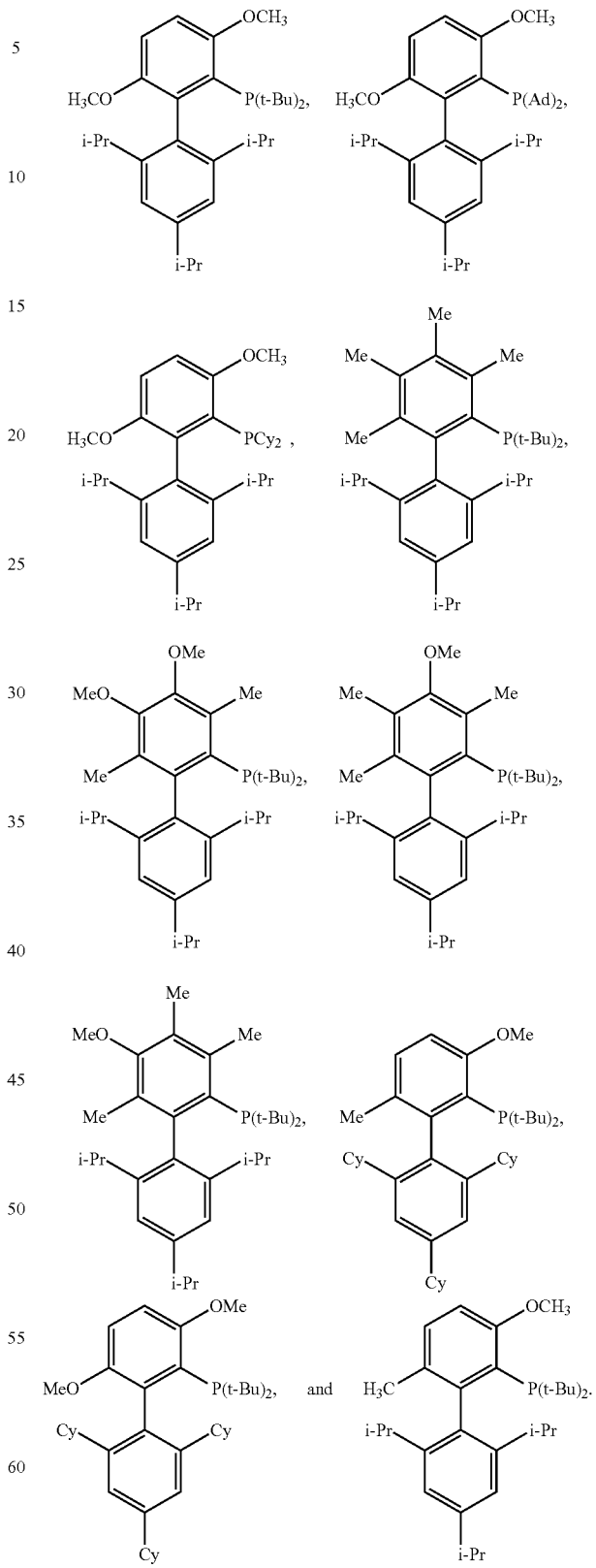
In certain embodiments, the invention relates to a compound of any one of the following structures:

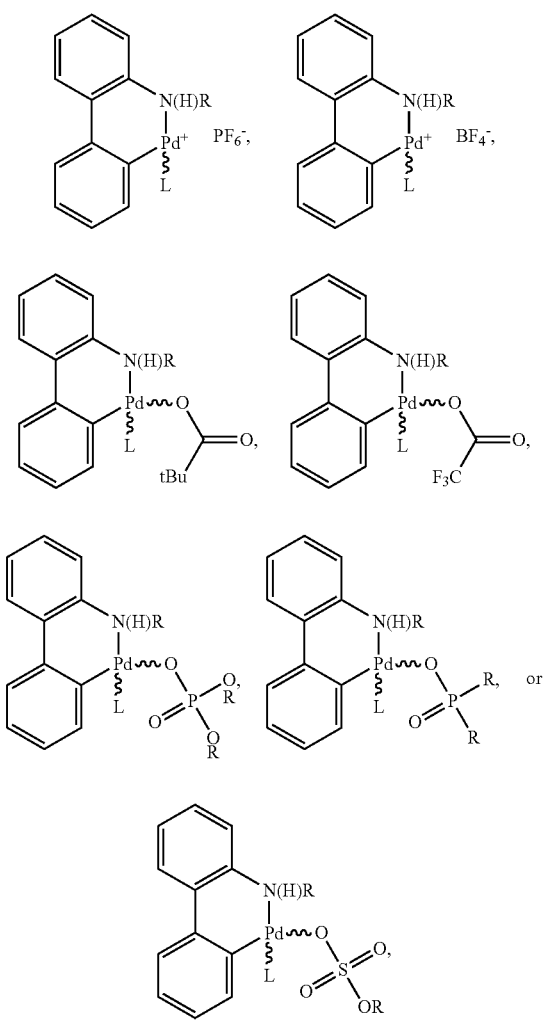

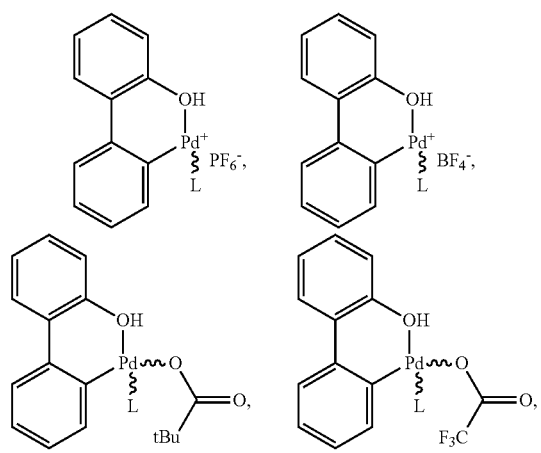

wherein

R is H, alkyl, or aryl; and

L is any one of the aforementioned ligands.

In certain embodiments, the invention relates to a compound of any one of the following structures:

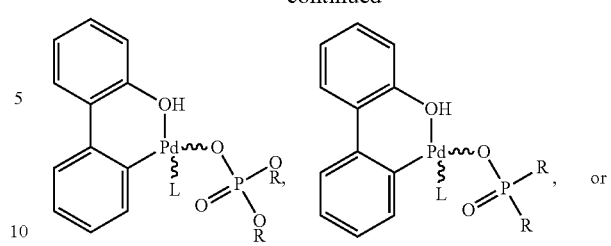

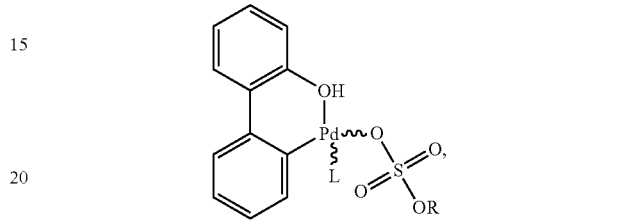

wherein

R is H, alkyl, or aryl; and

L is any one of the aforementioned ligands.

In certain embodiments, the invention relates to a compound of any one of the following structures:

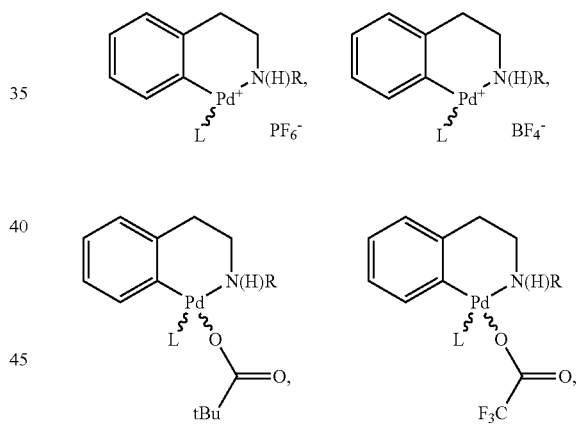

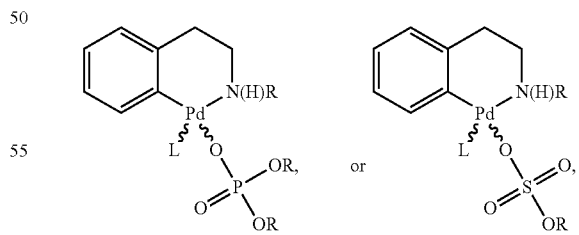

wherein

R is H, alkyl, or aryl; and

L is any one of the aforementioned ligands.

Dimers of the Invention

In certain embodiments, the invention relates to a dimer of formula IX

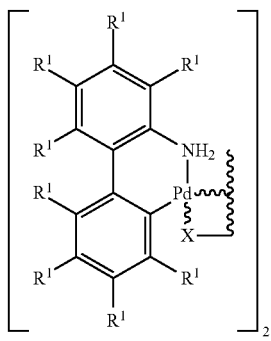

IX wherein, independently for each occurrence,
X is a non-coordinating anion; and
$R^1$ is H, alkyl, haloalkyl, hydroxy, alkoxy, aryloxy, aryl, or halo.

In certain embodiments, the invention relates to a dimer of formula X

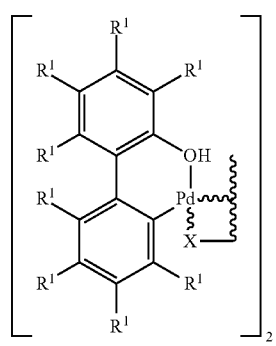

X wherein, independently for each occurrence,
X is a non-coordinating anion; and
$R^1$ is H, alkyl, haloalkyl, hydroxy, alkoxy, aryloxy, aryl, or halo.

In certain embodiments, the invention relates to a dimer of formula XI

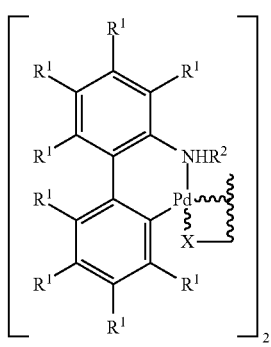

XI wherein, independently for each occurrence,
X is a non-coordinating anion; and
$R^1$ is H, alkyl, haloalkyl, hydroxy, alkoxy, aryloxy, aryl, or halo; and
$R^2$ is alkyl, haloalkyl or aryl.

In certain embodiments, the invention relates to a dimer of formula XII

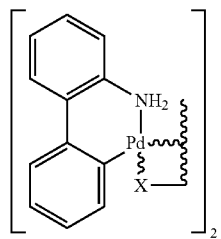

XII wherein X is a non-coordinating anion.

In certain embodiments, the invention relates to a dimer of formula XIII

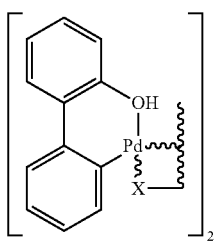

XIII wherein X is a non-coordinating anion.

In certain embodiments, the invention relates to a dimer of formula XIV

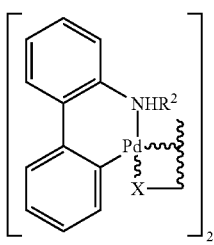

XIV wherein
X is a non-coordinating anion; and
$R^2$ is alkyl, haloalkyl or aryl.

In certain embodiments, the invention relates to a dimer of formula XV

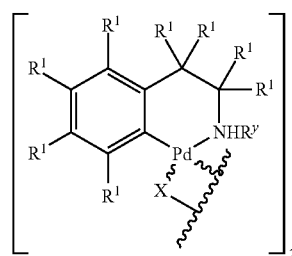

XV wherein, independently for each occurrence,
X is a non-coordinating anion; and
$R^1$ is H, alkyl, haloalkyl, hydroxy, alkoxy, aryloxy, aryl, or halo; and
$R^y$ is H, alkyl, haloalkyl or aryl.

In certain embodiments, the invention relates to a dimer of formula XVI

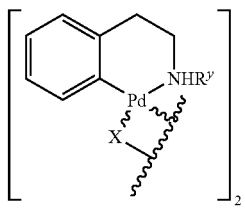

XVI wherein
X is a non-coordinating anion; and
$R^y$ is H, alkyl, haloalkyl or aryl.

In certain embodiments, the invention relates to any one of the aforementioned dimers, wherein X is selected from the group consisting of boron tetrafluoride, tetraarylborates (such as $B(C_6F_5)_4^-$ and $(B[3,5-(CF_3)_2C_6H_3]_4)^-$), hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

In certain embodiments, the invention relates to any one of the aforementioned dimers, wherein X is alkylsulfonate; and the alkyl is substituted alkyl. In certain embodiments, the invention relates to any one of the aforementioned dimers, wherein X is alkylsulfonate; and the alkyl is unsubstituted alkyl.

In certain embodiments, the invention relates to any one of the aforementioned dimers, wherein X is alkylsulfonate; and the alkyl is methyl, ethyl, propyl, or butyl. In certain embodiments, the invention relates to any one of the aforementioned dimers, wherein X is alkylsulfonate; and the alkyl is methyl or ethyl.

In certain embodiments, the invention relates to any one of the aforementioned dimers, wherein X is haloalkylsulfonate. In certain embodiments, the invention relates to any one of the aforementioned dimers, wherein X is fluoroalkylsulfonate.

In certain embodiments, the invention relates to any one of the aforementioned dimers, wherein X is fluoromethylsulfonate. In certain embodiments, the invention relates to any one of the aforementioned dimers, wherein X is trifluoromethylsulfonate.

In certain embodiments, the invention relates to any one of the aforementioned dimers, wherein X is cycloalkylalkylsulfonate. In certain embodiments, the invention relates to any one of the aforementioned dimers, wherein X is

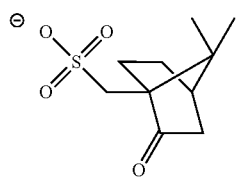

or its enantiomer.

In certain embodiments, the invention relates to any one of the aforementioned dimers, wherein X is arylsulfonate; and the aryl is substituted aryl. In certain embodiments, the invention relates to any one of the aforementioned dimers, wherein X is arylsulfonate; and the aryl is unsubstituted aryl.

In certain embodiments, the invention relates to any one of the aforementioned dimers, wherein X is phenylsulfonate. In certain embodiments, the invention relates to any one of the aforementioned dimers, wherein X is methylphenylsulfonate. In certain embodiments, the invention relates to any one of the aforementioned dimers, wherein X is p-toluenesulfonate.

In certain embodiments, the invention relates to any one of the aforementioned dimers, wherein $R^1$ is H or alkyl. In certain embodiments, the invention relates to any one of the aforementioned dimers, wherein $R^1$ is H.

In certain embodiments, the invention relates to any one of the aforementioned dimers, wherein $R^2$ is substituted alkyl. In certain embodiments, the invention relates to any one of the aforementioned dimers, wherein $R^2$ is unsubstituted alkyl.

In certain embodiments, the invention relates to any one of the aforementioned dimers, wherein $R^2$ is methyl, ethyl, propyl, or butyl.

In certain embodiments, the invention relates to any one of the aforementioned dimers, wherein $R^2$ is substituted aryl. In certain embodiments, the invention relates to any one of the aforementioned dimers, wherein $R^2$ is unsubstituted aryl.

In certain embodiments, the invention relates to any one of the aforementioned dimers, wherein $R^2$ is phenyl.

Methods of the Invention

In certain embodiments, the invention relates to a method of Scheme 1:

Scheme 1

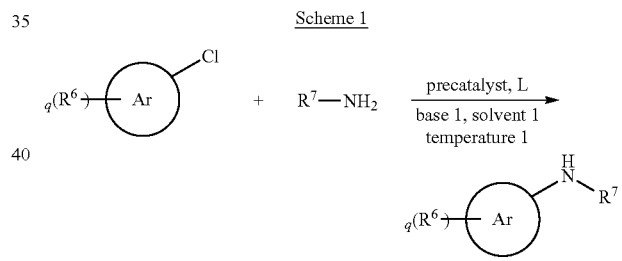

wherein,
the precatalyst is any one of the aforementioned precatalysts;
L is defined as above;
Ar is aryl or heteroaryl;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl; and
$R^7$ is aryl, heteroaryl, aralkyl, heteroaralkyl, alkyl, cycloalkyl.

In certain embodiments, the invention relates to any one of the aforementioned methods, wherein temperature 1 is from about 50° C. to about 150° C. In certain embodiments, the invention relates to any one of the aforementioned methods, wherein temperature 1 is about 55° C., about 60° C., about 65° C., about 70° C., about 75° C., about 80° C., about 85° C., about 90° C., about 95° C., about 100° C., about 105° C., about 110° C., about 115° C., about 120 C, about 125° C., about 130° C., about 135° C., about 140° C., or about 145° C.

In certain embodiments, the invention relates to a method of Scheme 2:

Scheme 2

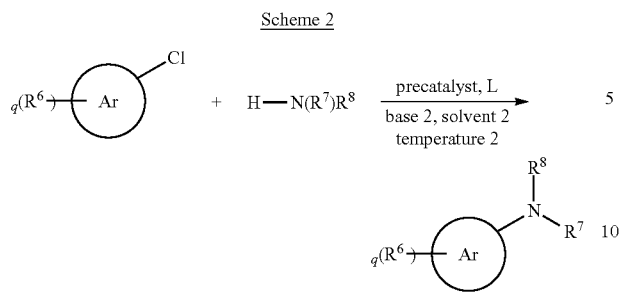

wherein,
the precatalyst is any one of the aforementioned precatalysts;
L is defined as above;
Ar is aryl or heteroaryl;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl;
$R^7$ is alkyl, aralkyl, aryl, or heteroaryl; and
$R^8$ is alkyl, aralkyl, aryl, or heteroaryl, or, $R^7$ and $R^8$, taken together, form a cycloalkyl or heterocycloalkyl ring;

In certain embodiments, the invention relates to any one of the aforementioned methods, wherein temperature 2 is from about 40° C. to about 120° C. In certain embodiments, the invention relates to any one of the aforementioned methods, wherein temperature 2 is about 45° C., about 50° C., about 55° C., about 60° C., about 65° C., about 70° C., about 75° C., about 80° C., about 85° C., about 90° C., about 95° C., about 100° C., about 105° C., about 110° C., or about 115° C.

In certain embodiments, the invention relates to a method of Scheme 3:

Scheme 3

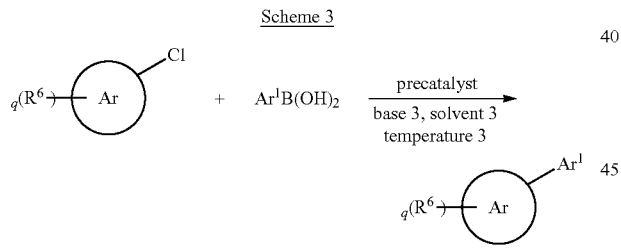

wherein,
the precatalyst is any one of the aforementioned precatalysts;
Ar is aryl or heteroaryl;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl; and
$Ar^1$ is aryl or heteroaryl.

In certain embodiments, the invention relates to any one of the aforementioned methods, wherein temperature 3 is from about 10° C. to about 60° C. In certain embodiments, the invention relates to any one of the aforementioned methods, wherein temperature 3 is about 15° C., about 20° C., about 25° C., about 30° C., about 35° C., about 40° C., about 45° C., or about 50° C.

In certain embodiments, the invention relates to a method of Scheme 4:

Scheme 4

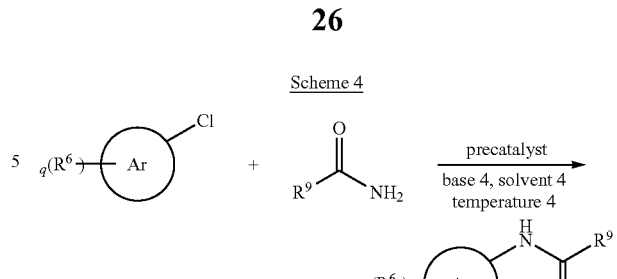

wherein,
the precatalyst is any one of the aforementioned precatalysts;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl; and
$R^9$ is aralkyl, heteroaralkyl, aryl, heteroaryl, or cycloalkyl.

In certain embodiments, the invention relates to any one of the aforementioned methods, wherein temperature 4 is from about 60° C. to about 160° C. In certain embodiments, the invention relates to any one of the aforementioned methods, wherein temperature 4 is about 65° C., about 70° C., about 75° C., about 80° C., about 85° C., about 90° C., about 95° C., about 100° C., about 105° C., about 110° C., about 115° C., about 120 C, about 125° C., about 130° C., about 135° C., about 140° C., about 145° C., about 150° C., or about 155° C.

In certain embodiments, the invention relates to a method of Scheme 5:

Scheme 5

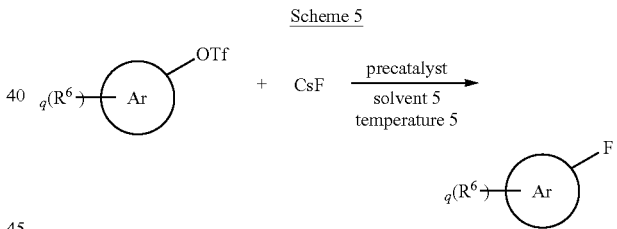

wherein,
the precatalyst is any one of the aforementioned precatalysts;
q is 0, 1, 2, 3, or 4; and
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl.

In certain embodiments, the invention relates to any one of the aforementioned methods, wherein temperature 5 is from about 70° C. to about 190° C. In certain embodiments, the invention relates to any one of the aforementioned methods, wherein temperature 5 is about 75° C., about 80° C., about 85° C., about 90° C., about 95° C., about 100° C., about 105° C., about 110° C., about 115° C., about 120 C, about 125° C., about 130° C., about 135° C., about 140° C., about 145° C., about 150° C., about 155° C., about 160° C., about 165° C., about 170° C., about 175° C., or about 180° C.

In certain embodiments, the invention relates to a method of Scheme 8:

Scheme 8

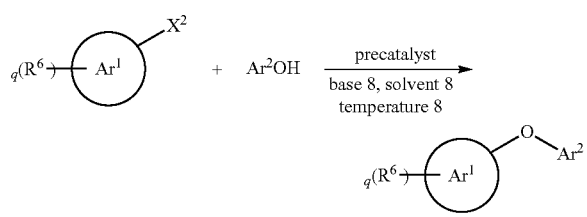

wherein, independently for each occurrence,
the precatalyst is any one of the aforementioned precatalysts;
$X^2$ is halo;
$Ar^1$ is aryl or heteroaryl;
$Ar^2$ is aryl or heteroaryl, which is optionally substituted with 1, 2, 3, or 4 $R^{11}$;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl; and
$R^{11}$ is alkoxy, alkyl ester, alkylcarbonyl, hydroxyalkyl, cyano, halo, amino, cycloalkyl, aryl, haloalkyl, nitro, hydroxy, alkoxy, aryloxy, alkyl, alkylthio, or cyanoalkyl.

In certain embodiments, the invention relates to any one of the aforementioned methods, wherein temperature 8 is from about 10° C. to about 90° C. In certain embodiments, the invention relates to any one of the aforementioned methods, wherein temperature 8 is about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., or about 90° C.

In certain embodiments, the invention relates to a method of Scheme 9:

Scheme 9

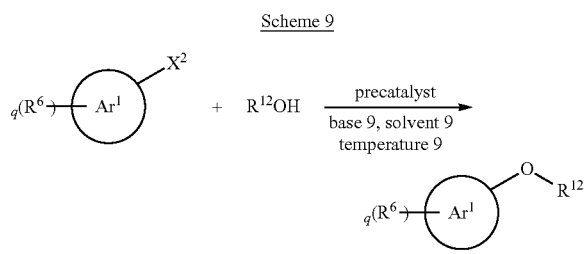

wherein, independently for each occurrence,
the precatalyst is any one of the aforementioned precatalysts;
$X^2$ is halo;
$Ar^1$ is aryl or heteroaryl;
q is 0, 1, 2, 3, or 4;
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl; and
$R^{12}$ is alkyl or substituted alkyl (including but not limited to aralkyl, fluoroalkylalkyl, or cycloalkylalkyl).

In certain embodiments, the invention relates to any one of the aforementioned methods, wherein temperature 9 is from about 50° C. to about 160° C. In certain embodiments, the invention relates to any one of the aforementioned methods, wherein temperature 9 is about 50° C., about 55° C., about 60° C., about 65° C., about 70° C., about 75° C., about 80° C., about 85° C., about 90° C., about 95° C., about 100° C., about 105° C., about 110° C., about 115° C., about 120 C, about 125° C., about 130° C., about 135° C., about 140° C., about 145° C., about 150° C., about 155° C., or about 160° C.

In certain embodiments, the invention relates to a method of Scheme 10:

Scheme 10

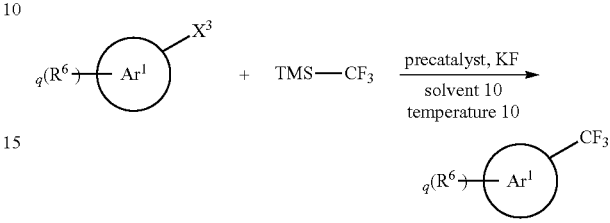

wherein, independently for each occurrence,
the precatalyst is any one of the aforementioned precatalysts;
$X^3$ is halo, triflate, or mesylate;
$Ar^1$ is aryl or heteroaryl;
q is 0, 1, 2, 3, or 4; and
$R^6$ is alkoxy, alkyl ester, alkylcarbonyl, hydroxyalkyl, cyano, halo, amino, cycloalkyl, aryl, haloalkyl, nitro, hydroxy, alkoxy, aryloxy, or alkyl.

In certain embodiments, the invention relates to any one of the aforementioned methods, wherein temperature 10 is from about 50° C. to about 160° C. In certain embodiments, the invention relates to any one of the aforementioned methods, wherein temperature 10 is about 50° C., about 55° C., about 60° C., about 65° C., about 70° C., about 75° C., about 80° C., about 85° C., about 90° C., about 95° C., about 100° C., about 105° C., about 110° C., about 115° C., about 120 C, about 125° C., about 130° C., about 135° C., about 140° C., about 145° C., about 150° C., about 155° C., or about 160° C.

In certain embodiments, the invention relates to any one of the aforementioned methods, wherein base 1, base 2, base 3, base 4, base 8, or base 9 comprises t-butoxy, carbonate, or phosphate.

In certain embodiments, the invention relates to any one of the aforementioned methods, wherein base 1, base 2, base 3, base 4, base 8, or base 9 is NaOt-Bu, $Cs_2CO_3$, $K_2CO_3$, or $K_3PO_4$.

In certain embodiments, the invention relates to any one of the aforementioned methods, wherein solvent 1, solvent 2, solvent 3, or solvent 4 is a non-polar solvent or a polar aprotic solvent.

In certain embodiments, the invention relates to any one of the aforementioned methods, wherein solvent 1, solvent 2, solvent 3, or solvent 4 is an ether or an alcohol.

In certain embodiments, the invention relates to any one of the aforementioned methods, wherein solvent 1, solvent 2, solvent 3, or solvent 4 comprises dioxane, tetrahydrofuran, water, or tBuOH.

In certain embodiments, the invention relates to any one of the aforementioned methods, wherein solvent 5 or solvent 9 is a non-polar solvent.

In certain embodiments, the invention relates to any one of the aforementioned methods, wherein solvent 5 or solvent 9 comprises toluene.

In certain embodiments, the invention relates to any one of the aforementioned methods, wherein solvent 8 is a non-polar solvent.

In certain embodiments, the invention relates to any one of the aforementioned methods, wherein solvent 8 comprises toluene. In certain embodiments, the invention relates to any one of the aforementioned methods, wherein solvent 8 comprises toluene and dimethoxyether.

In certain embodiments, the invention relates to any one of the aforementioned methods, wherein solvent 10 comprises dioxane and toluene. In certain embodiments, the invention relates to any one of the aforementioned methods, wherein solvent 10 comprises dioxane and toluene in a 1:1 ratio.

In certain embodiments, the invention relates to any one of the aforementioned methods, wherein the precatalyst is present in an amount from about 0.005 mol % to about 10 mol %.

In certain embodiments, the invention relates to any one of the aforementioned methods, wherein the precatalyst is present in about 0.005 mol %, about 0.01 mol %, about 0.05 mol %, about 0.1 mol %, about 0.5 mol %, about 1 mol %, about 2 mol %, about 3 mol %, about 4 mol %, or about 5 mol %.

In certain embodiments, the invention relates to any one of the aforementioned methods, wherein L is present in an amount from about 0.005 mol % to about 10 mol %.

In certain embodiments, the invention relates to any one of the aforementioned methods, wherein L is present in about 0.005 mol %, about 0.01 mol %, about 0.05 mol %, about 0.1 mol %, about 0.5 mol %, about 1 mol %, about 2 mol %, about 3 mol %, about 4 mol %, or about 5 mol %.

In certain embodiments, the invention relates to a method of making any one of the aforementioned dimers, according to Scheme 6a Scheme 6a

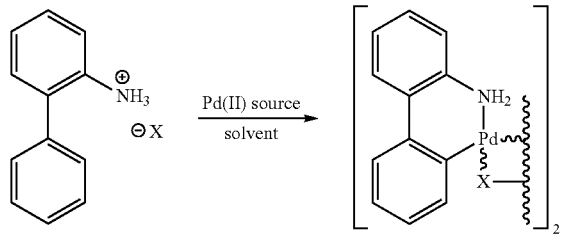

wherein X is a non-coordinating anion.

In certain embodiments, the invention relates to a method of making any one of the aforementioned dimers, according to Scheme 6b Scheme 6b

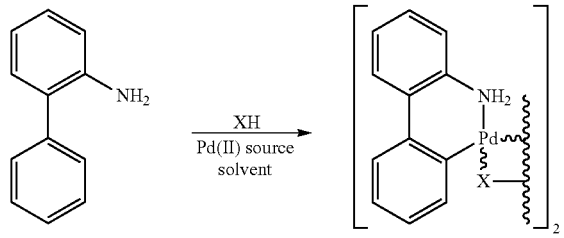

wherein X is a non-coordinating anion.

In certain embodiments, the invention relates to a method of making any one of the aforementioned dimers, according to Scheme 6c Scheme 6c

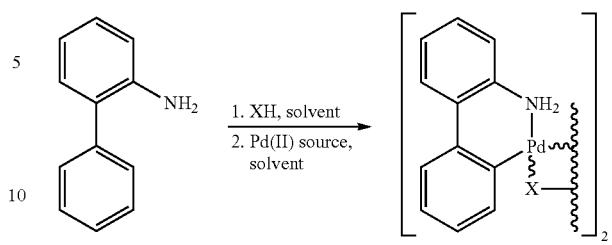

wherein X is a non-coordinating anion.

In certain embodiments, the invention relates to any one of the aforementioned methods, wherein the Pd(II) source is $Pd(OAc)_2$.

In certain embodiments, the invention relates to any one of the aforementioned methods, wherein the solvent is a non-polar solvent or a polar aprotic solvent. In certain embodiments, the invention relates to any one of the aforementioned methods, wherein the solvent is toluene. In certain embodiments, the invention relates to any one of the aforementioned methods, wherein the solvent is THF.

In certain embodiments, the invention relates to any one of the aforementioned methods, wherein the reaction takes place at from about 25° C. to about 75° C. In certain embodiments, the invention relates to any one of the aforementioned methods, wherein the reaction takes place at about 25° C., about 30° C., about 35° C., about 40° C., about 45° C., about 50° C., about 55° C., about 60° C., about 65° C., about 70° C., or about 75° C.

In certain embodiments, the invention relates to any one of the aforementioned methods, wherein the reaction is substantially complete after about 30 min, about 35 min, about 40 min, about 45 min, about 50 min, about 55 min, or about 60 min.

In certain embodiments, the invention relates to a method of making any one of the aforementioned precatalysts, according to Scheme 7

Scheme 7

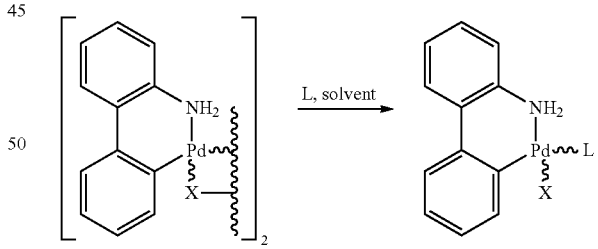

wherein
  X is a non-coordinating anion; and
  L is a ligand as defined above.

In certain embodiments, the invention relates to any one of the aforementioned methods, wherein the solvent is a polar aprotic solvent. In certain embodiments, the invention relates to any one of the aforementioned methods, wherein the solvent is THF or $CH_2Cl_2$.

In certain embodiments, the invention relates to any one of the aforementioned methods, wherein the reaction takes place at from about 10° C. to about 40° C. In certain embodiments, the invention relates to any one of the aforementioned methods, wherein the reaction takes place at about 15° C., about 20° C., about 25° C., about 30° C., or about 35° C.

In certain embodiments, the invention relates to any one of the aforementioned methods, wherein the reaction is substantially complete after about 10 min, about 15 min, about 20 min, about 25 min, about 30 min, about 35 min, about 40 min, about 45 min, about 50 min, about 55 min, about 60 min, about 65 min, about 70 min, about 75 min, about 80 min, about 85 min, or about 90 min. In certain embodiments, the invention relates to any one of the aforementioned methods, wherein the reaction is substantially complete after about 2 h, about 3 h, about 4 h, about 5 h, about 6 h, about 7 h, about 8 h, about 9 h, about 10 h, about 11 h, or about 12 h.

The reactions of the present invention may be performed under a wide range of conditions, though it will be understood that the solvents and temperature ranges recited herein are not limitative and only correspond to exemplary modes of the processes of the invention.

In general, it will be desirable that reactions are run using mild conditions which will not adversely affect the reactants, the precatalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran, water and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents, such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants or a ligand anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, precatalyst and solvent are also not generally critical to the success of the reaction, and may be accomplished in any conventional fashion. In an order of events that, in some cases, can lead to an enhancement of the reaction rate, the base, e.g., t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass-lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

DEFINITIONS

For convenience, before further description of the present invention, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths but with at least two carbon atoms. Preferred alkyl groups are lower alkyls. In preferred embodiments, a substituent designated herein as alkyl is a lower alkyl.

The term "aryl" as used herein includes 5-, 6- and 7-membered aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. Also, "DCM" stands for dichloromethane; "rt" stands for room temperature, and may mean about 20° C., about 21° C., about 22° C., about 23° C., about 24° C., about 25° C., or about 26° C.; "THF" stands for tetrahydrofuran; "BINAP" stands for 2,2'-bis(diphenylphosphino)-1,1'-binaphthyl; "dppf" stands for 1,1'-bis(diphenylphosphino)ferrocene; "dppb" stands for 1,4-bis(diphenylphosphinobutane; "dppp" stands for 1,3-bis(diphenylphosphino)propane; "dppe" stands for 1,2-bis(diphenylphosphino)ethane. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "non-coordinating anion" relates to a negatively charged moiety that interacts weakly with cations. Non-coordinating anions are useful in studying the reactivity of electrophilic cations, and are commonly found as counterions for cationic metal complexes with an unsaturated coordination sphere. In many cases, non-coordinating anions have a negative charge that is distributed symmetrically over a number of electronegative atoms. Salts of these anions are often soluble non-polar organic solvents, such as dichloromethane, toluene, or alkanes.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art recognized and refer to both unsubstituted and substituted amines, e.g., a moiety that can be represented by the general formula:

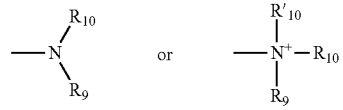

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$ ed.*; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms, such as nitrogen, may have hydrogen substituents and/or any permissible substituents of organic compounds described herein which satisfy the valencies of the heteroatoms.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention may be understood with reference to the following examples, which are presented for illustrative purposes only and which are non-limiting. The substrates utilized in these examples were either commercially available, or were prepared from commercially available reagents.

Example 1

Synthesis of Palladium Sulfonate Dimers

Figure 2:
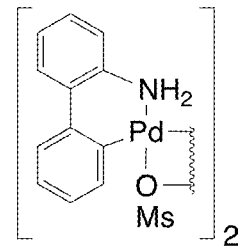
FIG. 2 depicts a palladium sulfonate dimer of the invention. The stereochemistry at Pd in the dimer is cis or trans.

2-Aminobiphenylpalladium Mesylate Dimer:
A 300-mL round-bottomed flask equipped with a magnetic stir bar and fitted with a rubber septum was charged with 2-ammoniumbiphenyl mesylate (7.89 g, 30.0 mmol, 1.00 eq) and palladium acetate (6.72 g, 30.0 mmol, 1.00 eq). The flask was evacuated and backfilled with argon (this sequence was repeated three times), after which 120 mL anhydrous toluene was added. The mixture was stirred at 50° C. for 45 min or until it became milky and off-white in appearance. After cooling to room temperature the suspension was filtered, washed with toluene (25 mL) and diethyl ether (3×25 mL), and dried under vacuum for 24 hours to afford the title compound as an off-white to tan solid. Yield: 10.2 g (92%). FIG. 2.

2-Aminobiphenylpalladium Ethanesulfonate Dimer

Figure 3:
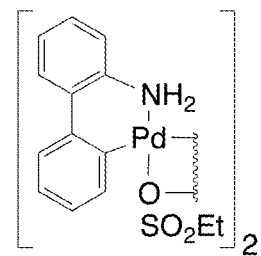
FIG. 3 depicts a palladium sulfonate dimer of the invention. The stereochemistry at Pd in the dimer is cis or trans.

A 50-mL round-bottomed flask equipped with a magnetic stir bar and fitted with a rubber septum was charged with 2-ammoniumbiphenyl ethanesulfonate (1.20 g, 4.30 mmol, 1.00 eq.) and palladium acetate (963 mg, 4.30 mmol, 1.00 eq). Then toluene (25 mL) was added by syringe and the mixture was heated at 50° C. for 45 minutes or it became a milky, off-white suspension. After cooling to room temperature the suspension was filtered and washed with diethyl ether (3×10 mL) and dried under vacuum to afford the title compound as a deep beige solid. Yield: 1.61 g, 98%. FIG. 3.

2-Aminobiphenylpalladium Camphorsulfonate Dimer

Figure 4:
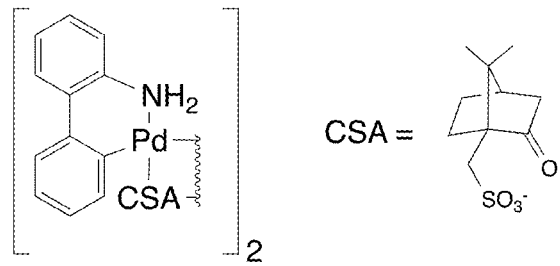
FIG. 4 depicts a palladium sulfonate dimer of the invention. The stereochemistry at Pd in the dimer is cis or trans.

A 50-mL round-bottomed flask equipped with a magnetic stir bar and bitted with a rubber septum was charged with 2-aminobiphenyl (338 mg, 2.00 mmol, 1.00 eq), (±)-10-camphorsulfonic acid (464 mg, 2.00 mmol, 1.00 eq.) and palladium acetate (448 mg, 2.00 mmol, 1.00 eq). Then toluene (20 mL) was added by syringe and the mixture was stirred at 50° C. for 45 minutes or until milky and off-white in appearance. After cooling to room temperature the suspension was filtered and washed with diethyl ether (3×10 mL) and dried under vacuum to afford the title compound as a tan solid. Yield: 677 mg, 67%. FIG. 4.

2-Aminobiphenylpalladium Tosylate Dimer

Figure 5:
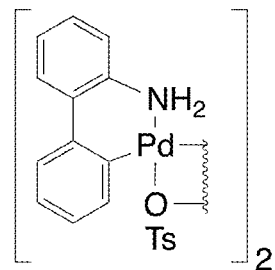
FIG. 5 depicts a palladium sulfonate dimer of the invention. The stereochemistry at Pd in the dimer is cis or trans.

A 24-mL test tube equipped with a magnetic stir bar and fitted with a teflon septum was charged with 2-aminobiphenyl (169 mg, 1.00 mmol, 1.00 eq) and p-toluenesulfonic acid monohydrate (192 mg, 1.00 mmol, 1.00 eq). The tube was sealed and then evacuated and backfilled with argon, followed by the addition of THF (5 mL). The resulting suspension was stirred at room temperature for 10 minutes, after which palladium acetate (224 mg, 1.00 mmol, 1.00 eq) was added and rinsed down the walls of the flask with the use of additional THF (2 mL). The mixture was then heated at 50° C. for 30 min, or until it became a homogenous yellow solution. After cooling to room temperature, the solution volume was reduced by 75% with the aid of a rotary evaporator, after which the product was precipitated with hexanes. The resulting solid was filtered and dried under vacuum for 24 hours to afford the title compound as a beige solid. Yield: 355 mg, 80%. FIG. 5.

Example 2

Synthesis of 2-Aminobiphenylpalladium Mesylate Precatalysts

Figure 6:
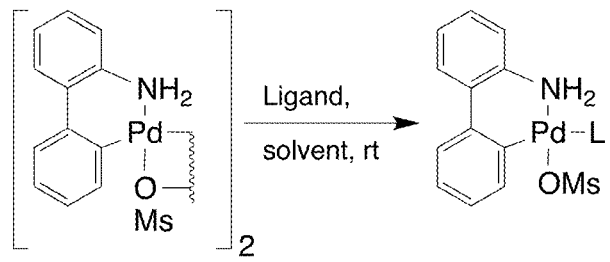
FIG. 6 depicts a general procedure to synthesize a 2-aminobiphenylpalladium mesylate precatalyst of the invention from a palladium sulfonate dimer of the invention. The stereochemistry at Pd in the precatalyst and in the dimer is cis or trans.

2-Aminobiphenylpalladium Mesylate Precatalyst General Procedure:
A test tube, equipped with a magnetic stir bar and fitted with a Teflon screw-cap, was charged with 2-aminobiphenylpalladium mesylate dimer (370 mg, 0.50 mmol, 0.50 eq) and ligand (1.00 mmol, 1.00 eq). THF or DCM (5 mL) was added by syringe and the reaction was stirred for 15 min to 1 h. The reaction progress was monitored by $^{31}P$ NMR, observing the disappearance of free ligand signal and appearance of the precatalyst signal downfield. After completion, the reaction mixture was transferred to a scintillation vial and the solvent was removed under vacuum at room temperature until ~10% remained. The residue was then triturated with pentane. The resulting solid was isolated via filtration and further dried under vacuum. FIG. 6.

2-Aminobiphenylpalladium Mesylate XPhos Precatalyst (Representative Procedure)

Figures 7, 8:
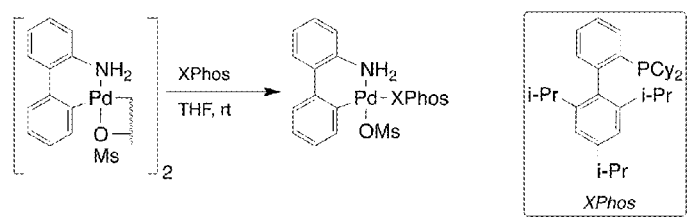
FIG. 7 depicts an exemplary synthesis of a 2-aminobiphenylpalladium mesylate precatalyst from a palladium sulfonate dimer of the invention. The stereochemistry at Pd in the precatalyst and in the dimer is cis or trans.
FIG. 8 tabulates as function of the ligand used the yields of various 2-aminobiphenylpalladium mesylate precatalysts of the invention formed from the corresponding palladium sulfonate dimer.

A 300-mL round-bottomed flask equipped with a stir bar and rubber septum was charged with μ-OMs dimer 3 (11.92 g, 15.25 mmol, 0.50 eq) and XPhos (14.52 g, 30.5 mmol, 1.00 eq). The flask was evacuated under vacuum and backfilled with argon (this procedure was repeated twice), after which THF (120 mL) was added. The reaction mixture was stirred at room temperature for 45 min. After removal of 90% of the solvent under vacuum the product was precipitated from pentane to afford the title compound as an off-white solid as the 1:1 THF complex. THF could be removed by dissolving the solid in DCM and reprecipitating with pentane. Yield: 25.5 g, 92%. FIG. 7.

FIG. 8 tabulates the % yield of various precatalysts formed using the procedures outlined above.

Example 3

Synthesis of 2-Aminobiphenylpalladium Triflate Precatalysts

Figure 9:
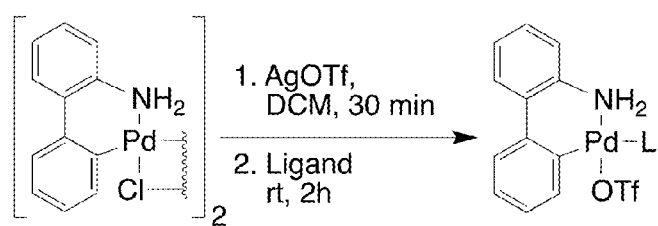
FIG. 9 depicts an exemplary synthesis of a 2-aminobiphenylpalladium triflate precatalyst from a palladium triflate dimer of the invention. The stereochemistry at Pd in the precatalyst and in the dimer is cis or trans.
Figure 10:
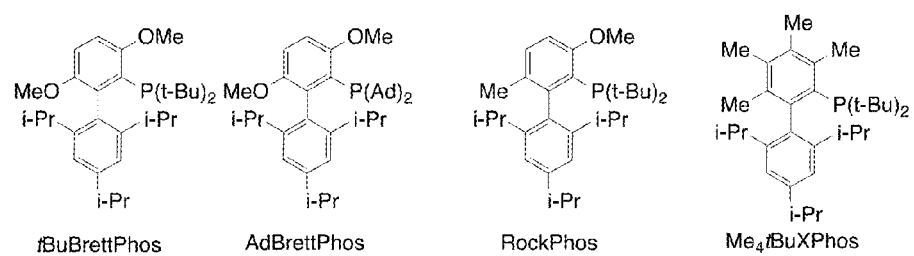
FIG. 10 depicts various ligands that may be used to prepare the precatalysts of the invention (tBuBrettPhos=L15; AdBrettPhos=L16; RockPhos=L17).
Figure 11:
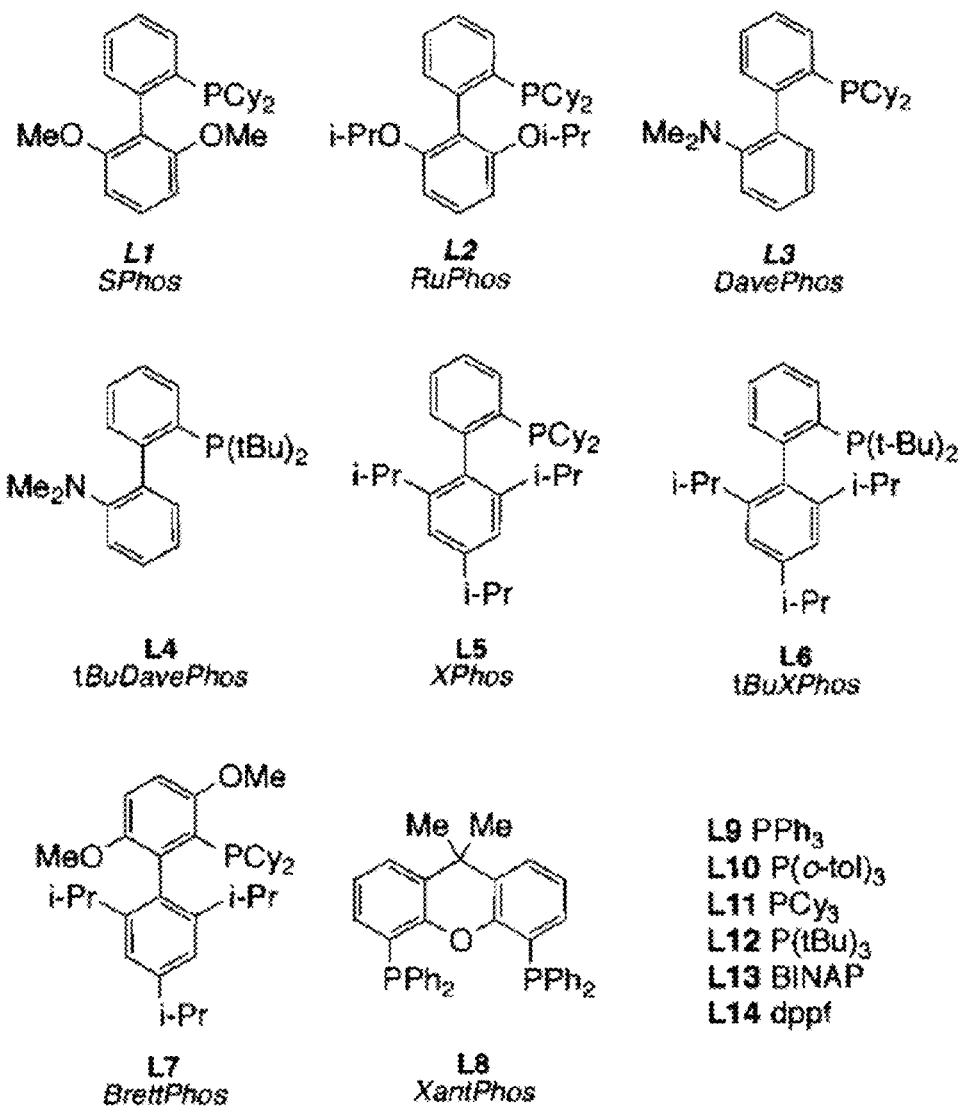
FIG. 11 depicts various ligands that may be used to prepare the precatalysts of the invention.
Figure 12:
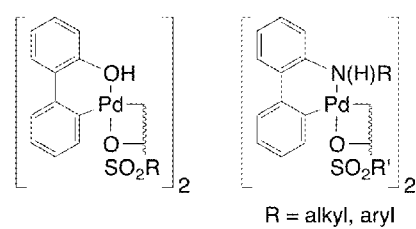
FIG. 12 depicts two palladium sulfonate dimers of the invention. The stereochemistry at Pd in the dimers is cis or trans.
Figure 13:
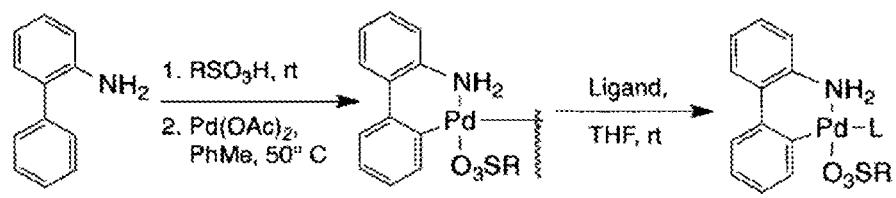
FIG. 13 depicts an exemplary synthesis of a 2-aminobiphenylpalladium sulfonate precatalyst from [1,1'-biphenyl]-2-amine. The stereochemistry at Pd in the precatalyst and in the dimer is cis or trans.

2-Aminobiphenylpalladium Triflate tBuBrettPhos Precatalyst:
A 250-mL round-bottomed flask equipped with a stirbar was charged with 2-aminobiphenylpalladium chloride dimer (3.41 g, 5.5 mmol, 0.50 eq) and silver triflate (2.82 g, 11 mmol, 1.00 eq.) and shielded from light. Then dichloromethane (100 mL) was added and the mixture was stirred at room temperature for 30 min. The suspension was then filtered through a wet pad of Celite into a 500-mL round-bottomed flask equipped with a stir bar containing tBu- BrettPhos (5.33 g, 11 mmol, 1.00 eq). An additional portion of dichloromethane (50 mL) was used to rinse the first flask and elute the mixture through the Celite plug. The resulting mixture was stirred at room temperature for 2 h, until becoming deep red in color. After removing ~90% of the solvent via rotary evaporation, pentane (200 mL) was added to precipitate the precatalyst. The suspension was sonicated for 30 minutes, crushed with a spatula and filtered. The resulting solid was dried under vacuum overnight to give the title compound as a dark orange solid. Yield: 9.59 g, 96%. FIG. 9.

Example 4

General Procedure for Catalyzed Arylation of Primary Amines

Figure 14:
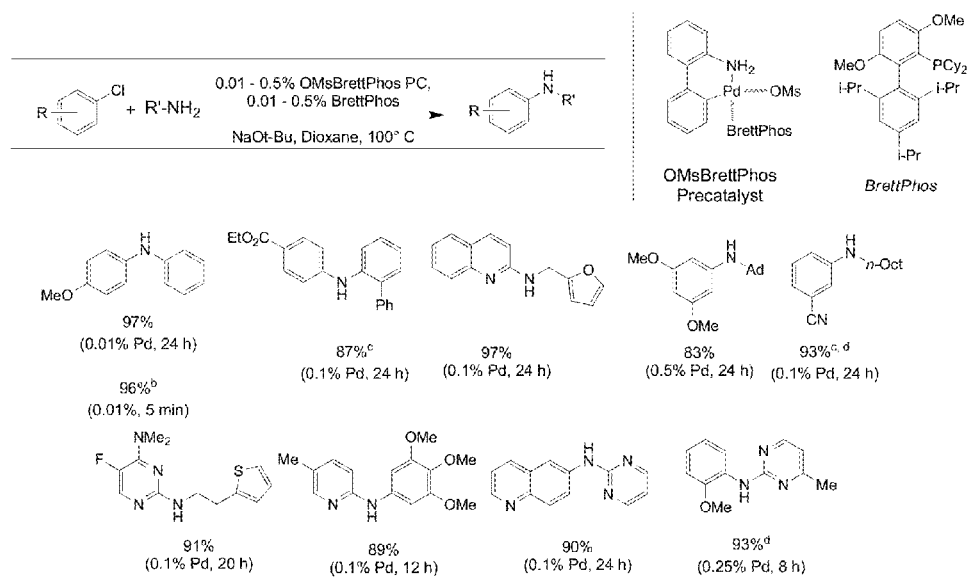
FIG. 14 depicts the arylation of primary amines using a precatalyst of the invention. Reaction conditions: aryl chloride (1 mmol), amine (1.2 mmol), NaOt-Bu, (1.2 mmol), OMsBrettPhos precatalyst (0.01-0.5%), BrettPhos ligand (0.01-0.5%), dioxane (1 mL) 100° C.; $^b$aryl iodide (1 mmol), amine (1.4 mmol), NaOt-Bu, (1.4 mmol), toluene (1 mL) 100° C.; $^c$Cs$_2$CO$_3$ was used as the base; $^d$t-BuOH was used as the solvent. Yields represent an average isolated yield based on at least two runs.

An oven-dried, resealable tube equipped with a magnetic stir bar and Teflon septum was charged with OMsBrettPhos precatalyst (0.01-0.5 mol %), BrettPhos (0.01-0.5 mol %) NaOt-Bu (115 mg, 1.20 mmol, 1.20 eq), aryl halide (1.00 mmol, 1.00 eq) and amine (1.20 mmol, 1.20 eq) if they are solids. The tube was evacuated and backfilled with argon. This process was repeated three times. Then the aryl halide and amine were added if they are liquid, followed by dioxane (1 mL). The reaction was heated at 100° C. and monitored by thin-layer chromatography or gas chromatography, observing the disappearance of aryl halide. After completion the reaction was cooled to room temperature, diluted with ethyl acetate, and filtered through a plug of Celite. The solvent was removed via rotary evaporation and the crude product was then purified by flash chromatography. See FIG. 14.

Example 5

General Procedure for Catalyzed Arylation of Secondary Amines

Figure 15:
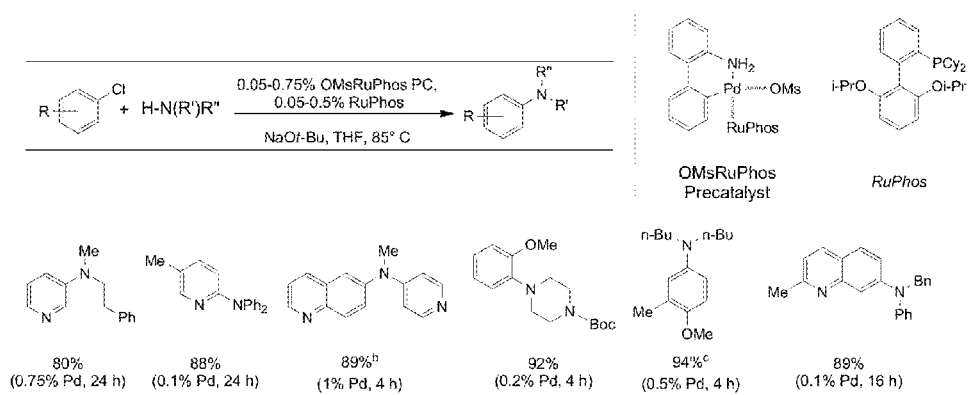
FIG. 15 depicts the arylation of secondary amines using a precatalyst of the invention. Reaction conditions: aryl chloride (1 mmol), amine (1.2 mmol), NaOt-Bu, (1.2 mmol), THF (1 mL) 85° C.; $^b$OMsXPhos precatalyst and XPhos was used; $^c$ArBr was used. Yields represent an average isolated yield based on two runs.

An oven-dried resealable tube equipped with a stir bar and Teflon septum was charged with OMsRuPhos precatalyst (0.01-1 mol %), RuPhos (0.01-1 mol %) NaOtBu (115 mg, 1.20 mmol, 1.20 eq), aryl halide (1.00 mmol) and amine (1.20 mmol, 1.20 eq) if they are solids. The tube was evacuated and backfilled with argon. This was repeated three times. Then the aryl halide and amine are added if they are liquid followed by THF (1 mL). The reaction was heated at 85° C. and monitored by thin-layer chromatography or gas chromatography, observing the disappearance of aryl halide. After completion the reaction was cooled to room temperature, diluted with ethyl acetate, and filtered through a plug of Celite. The solvent was removed via rotary evaporation and the crude product was then purified by flash chromatography. See FIG. 15.

Example 6

General Procedure for Suzuki-Miyaura Coupling of Unstable Boronic Acids

Figure 16:
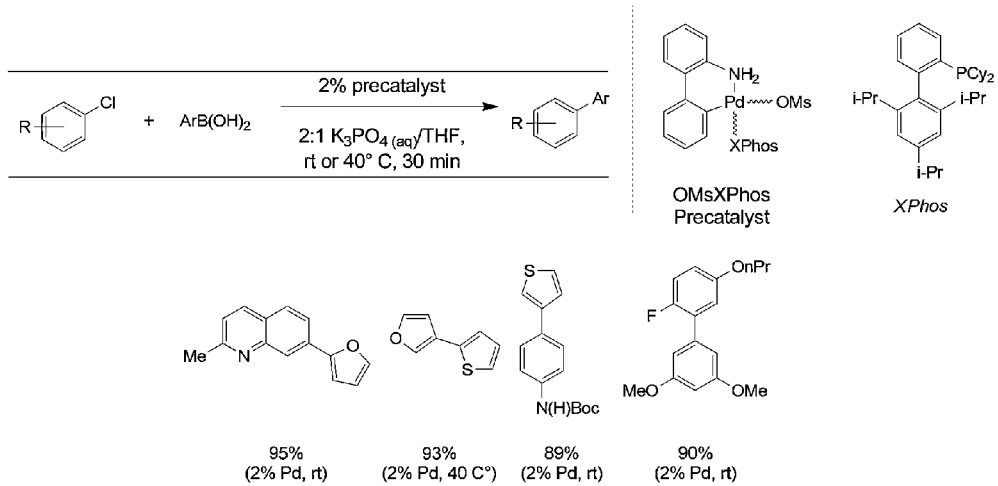
FIG. 16 depicts Suzuki-Miyaura coupling of unstable boronic acids using a precatalyst of the invention. Reaction conditions: aryl chloride (1 mmol), boronic acid (1.5 mmol), precatalyst (2%), THF (2 mL), 0.5 M K$_3$PO$_4$ (4 mL). Yields represent an average isolated yield based on two runs.

A resealable tube equipped with a magnetic stir bar and Teflon septum was charged with OMsXPhos precatalyst (2 mol %), the aryl halide (1 mmol) (if a solid), and the boronic acid (1.5 mmol). The tube was then evacuated and backfilled with argon. This process was repeated three times. Then the aryl halide (if a liquid) was added followed by THF (2 mL) and degassed 0.5 M $K_3PO_4$ solution (4 mL). The reaction was then stirred at rt or 40° for 30 min. The reaction mixture was diluted with water (10 mL) and ethyl acetate (10 mL) and the layers are separated. The aqueous layer was extracted with ethyl acetate three times. The combined organic phases are dried over magnesium sulfate, concentrated under vacuum and purified via column chromatography. See FIG. 16

Example 7

General Procedure for Arylation of Primary Amides

Figure 17:
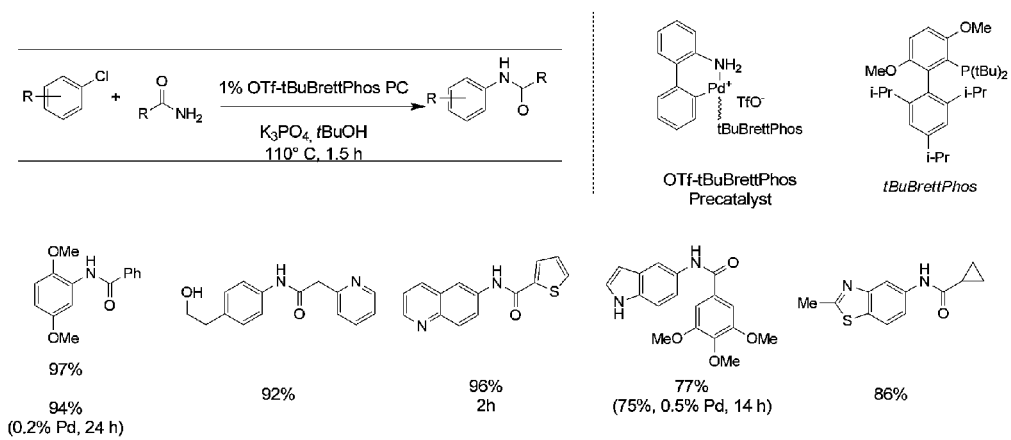
FIG. 17 depicts the arylation of primary amides using a precatalyst of the invention. Reaction conditions: aryl chloride (1 mmol), amide (1.2 mmol), K$_3$PO$_4$ (1.4 mmoll), precatalyst (1 mol %), tBuOH (2 mL), 110° C., 1.5 h. Yield represents an average isolated yield based on two runs.

An oven-dried, resealable tube equipped with a magnetic stir bar and Teflon septum was charged with OTf-tBu-BrettPhos precatalyst (9.1 mg, 1 mol %), $K_3PO_4$ (297 mg, 1.40 mmol, 1.40 eq), aryl halide (1.00 mmol, 1.00 eq) and amide (1.20 mmol, 1.20 eq) if they are solids. The tube was sealed and evacuated and backfilled with argon. This process was repeated three times. Then the aryl halide and amide were added if they are liquids, followed by tBuOH (2 mL). The reaction was heated at 110° C. and monitored by thin-layer chromatography or gas chromatography, observing the disappearance of aryl halide. After completion, the reaction was cooled to room temperature and diluted with ethyl acetate and water. The phases were separated and the aqueous phase was back extracted with ethyl acetate (2×5 mL). The combined organic phases were dried over sodium sulfate, concentrated via rotary evaporation and the crude product was purified by column chromatography. See FIG. 17.

Example 8

General Procedure for Fluorination of Aryl Triflates

Figure 18:
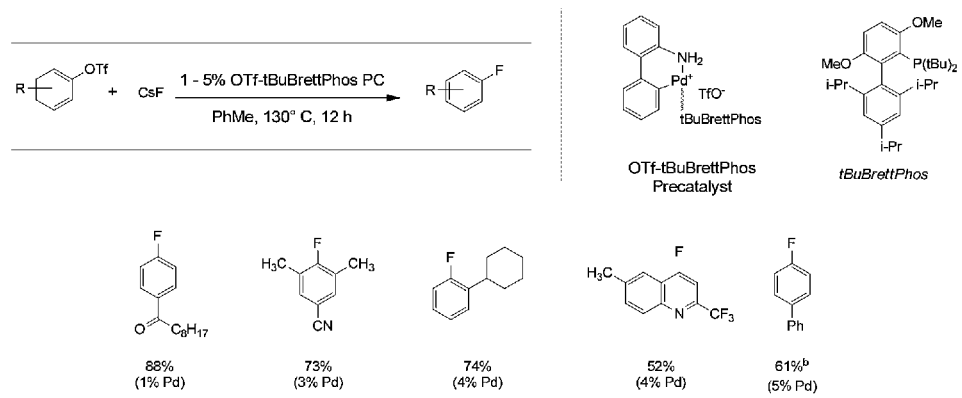
FIG. 18 depicts the fluorination of aryl triflates using a precatalyst of the invention. Reaction conditions: aryl triflate (1 mmol), cesium fluoride (2 mmol), toluene (5 mL) 130° C.; $^b$cyclohexane (5 mL), 120° C. Yield represents an average isolated yield based on two runs.

In a nitrogen filled glovebox an oven-dried resealable tube equipped with a stir bar was charged with (in this order) CsF (2.0 mmol, 2.0 eq.), OTf-tBuBrettPhos precatalyst (1-5%), aryl triflate (1.0 mmol, 1.0 eq.), and toluene (5 mL). The tube was sealed with a Teflon septum and removed from the glovebox, and the reaction mixture was stirred at 120-130° C. overnight. The reaction mixture was then allowed to cool to room temperature, filtered through celite eluting with $Et_2O$, and concentrated via rotary evaporation. The crude product was purified by flash chromatography. See FIG. 18.

Example 9

Synthesis of 2-Aminobiphenylpalladium Hexafluorophosphate Precatalysts

Figure 19:
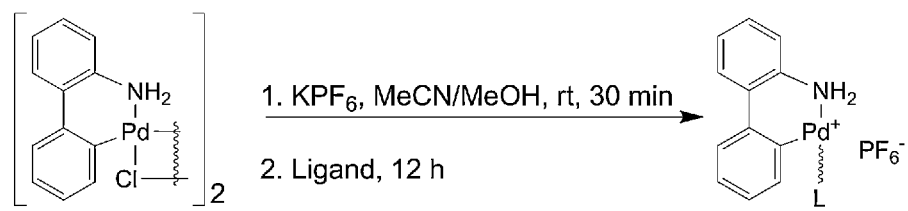
FIG. 19 depicts an exemplary synthesis of a 2-aminobiphenylpalladium hexafluorophosphate precatalyst from a dimer. The stereochemistry at Pd in the precatalyst and in the dimer is cis or trans.

A test tube, equipped with a magnetic stir bar and fitted with a Teflon screw-cap, was charged with μ-Cl dimer (78 mg, 0.125 mmol, 0.50 eq) and $KPF_6$ (276 mg, 1.50 mmol, 3.00 eq). The tube was sealed and evacuated and backfilled with argon (this was repeated two times), after which acetonitrile (3 mL) and methanol (1 mL) was added. After stirring for 30 min, XPhos (238 mg, 0.50 mmol, 1.00 eq) was added and rinsed down the sides of the tube with additional acetonitrile and the mixture was stirred overnight. After completion, the reaction mixture was eluted through celite and the solvent was removed via rotary evaporation. The residue was then triturated with pentane. The resulting solid was isolated via filtration and further dried under vacuum. See FIG. 19.

Example 10

Synthesis of 2-Aminobiphenylpalladium Tetrafluoroborate Precatalysts

Figure 20:
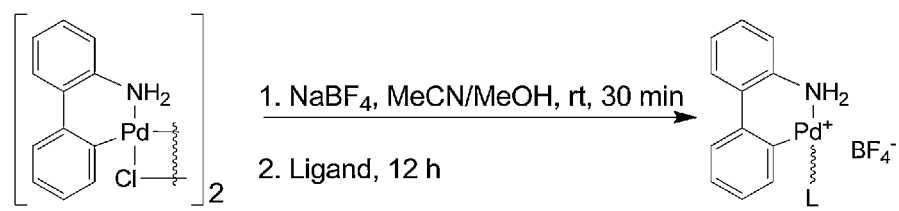
FIG. 20 depicts an exemplary synthesis of a 2-aminobiphenylpalladium tetrafluoroborate precatalyst from a dimer. The stereochemistry at Pd in the precatalyst and in the dimer is cis or trans.

A test tube, equipped with a magnetic stir bar and fitted with a Teflon screw-cap, was charged with μ-Cl dimer (78 mg, 0.125 mmol, 0.50 eq) and NaBF$_4$ (165 mg, 1.50 mmol, 3.00 eq). The tube was sealed and evacuated and backfilled with argon (this was repeated two times), after which acetonitrile (3 mL) and methanol (1 mL) was added. After stirring for 30 min, XPhos (238 mg, 0.50 mmol, 1.00 eq) was added and rinsed down the sides of the tube with additional acetonitrile and the mixture was stirred overnight. After completion, the reaction mixture was eluted through celite and the solvent was removed via rotary evaporation. The residue was then triturated with pentane. The resulting solid was isolated via filtration and further dried under vacuum. See FIG. 20.

Example 11

Synthesis of N-Phenyl-2-aminobiphenylpalladium Mesylate Precatalysts

N-phenyl-[1,1'-biphenyl]-2-ammonium Mesylate:
A 50 mL round-bottomed flask equipped with a stir bar was charged with 2-(N-phenyl)aminobiphenyl (1.09 g, 4.4 mmol, 1.00 eq) and diethyl ether (25 mL). Methanesulfonic acid (285 µL, 4.4 mmol, 1.00 eq) was added dropwise and the reaction mixture was stirred for 30 minutes. The solvent was then removed via rotary evaporation and the product was further dried under vacuum to yield the title compound as a green oil.

N-Phenyl-2-aminobiphenylpalladium Mesylate Dimer

A 24 mL screw-top tube equipped with a stir bar was charged with palladium acetate (1.00 g, 4.48 mmol, 1.00 eq) and a solution of N-phenyl-[1,1'-biphenyl]-2-ammonium mesylate (1.48 g, 4.48 mmol, 1.00 eq) in THF (10 mL). The reaction mixture was stirred at 50° C. for 15 minutes, until a yellow precipitate formed. After cooling to room temperature the solid was filtered and washed with diethyl ether (2×10 mL) and pentane (2×10 mL) and further dried under vacuum to afford the title compound as a yellow solid. Yield: 1.4 g, 65%.

N-Phenyl-2-aminobiphenylpalladium Mesylate Precatalyst (Representative Procedure with XPhos)

Figure 21:
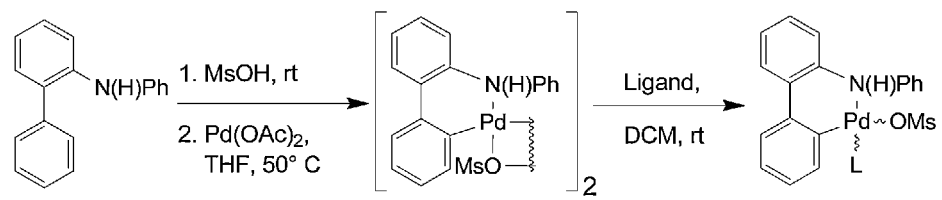
FIG. 21 depicts an exemplary synthesis of a precatalyst from N-phenyl-[1,1'-biphenyl]-2-amine. The stereochemistry at Pd in the precatalyst and in the dimer is cis or trans.
Figure 22:
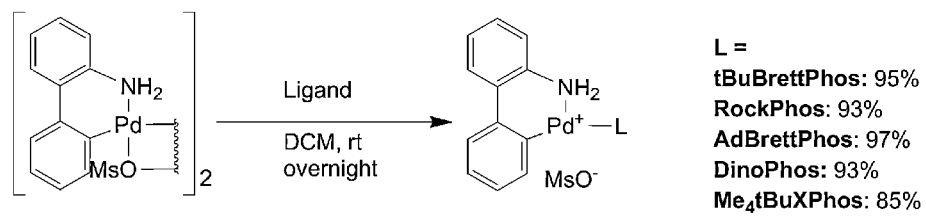
FIG. 22 depicts an exemplary synthesis of various precatalysts of the invention. The stereochemistry at Pd in the precatalyst and in the dimer is cis or trans.
Figure 22:
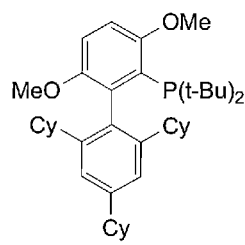
Figure 23:
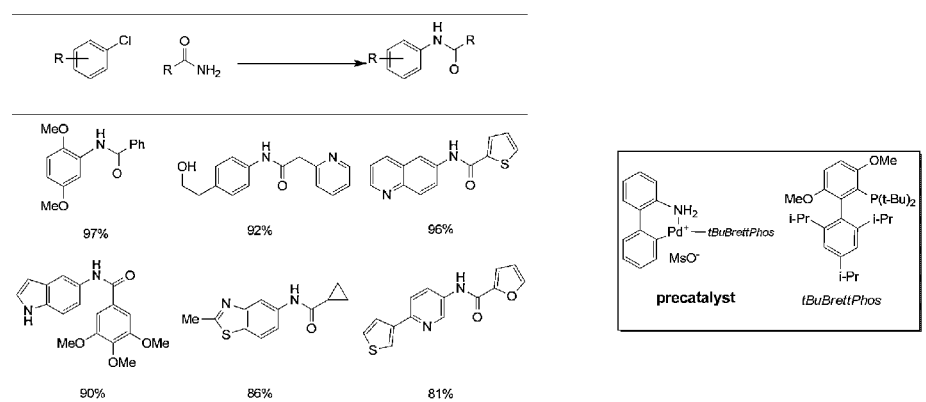
FIG. 23 depicts the amidation of aryl chlorides using a precatalyst of the invention. Reaction conditions: K$_3$PO$_4$ and 1% precatalyst, in tBuOH at 110° C.
Figure 24:
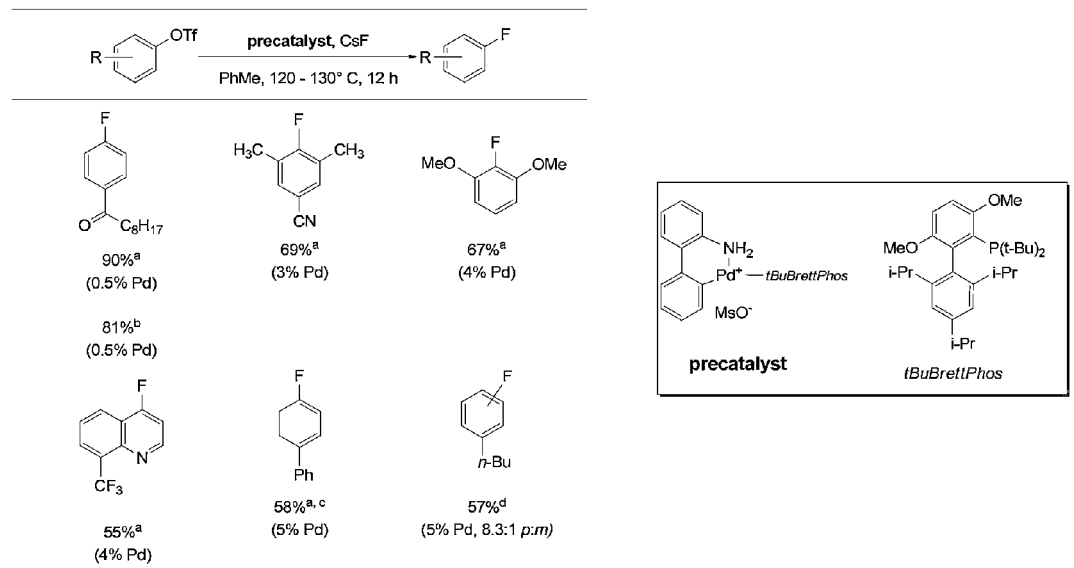
FIG. 24 depicts the fluorination of aryl triflates using a precatalyst of the invention.
Figure 25:
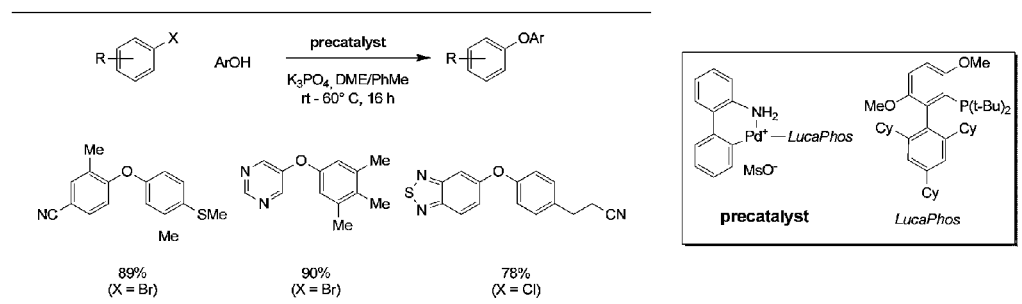
FIG. 25 depicts the arylation of phenols using a precatalyst of the invention.
Figure 26:
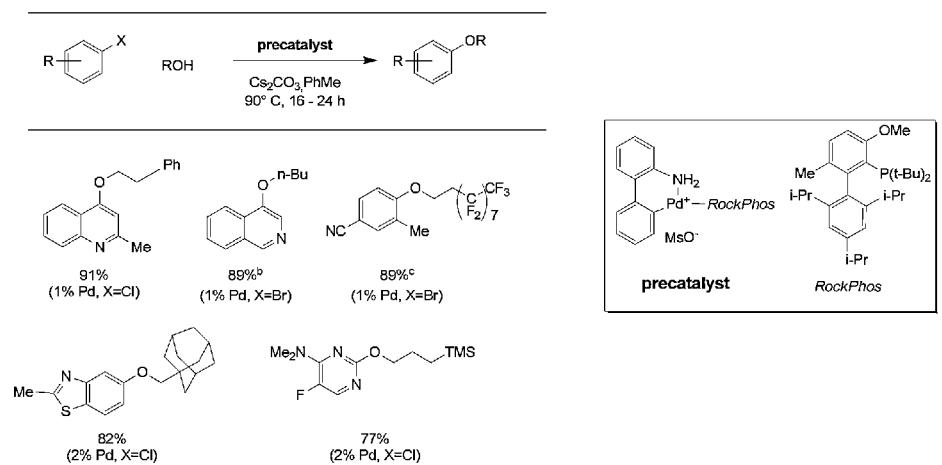
FIG. 26 depicts the arylation of alcohols using a precatalyst of the invention.
Figure 27:
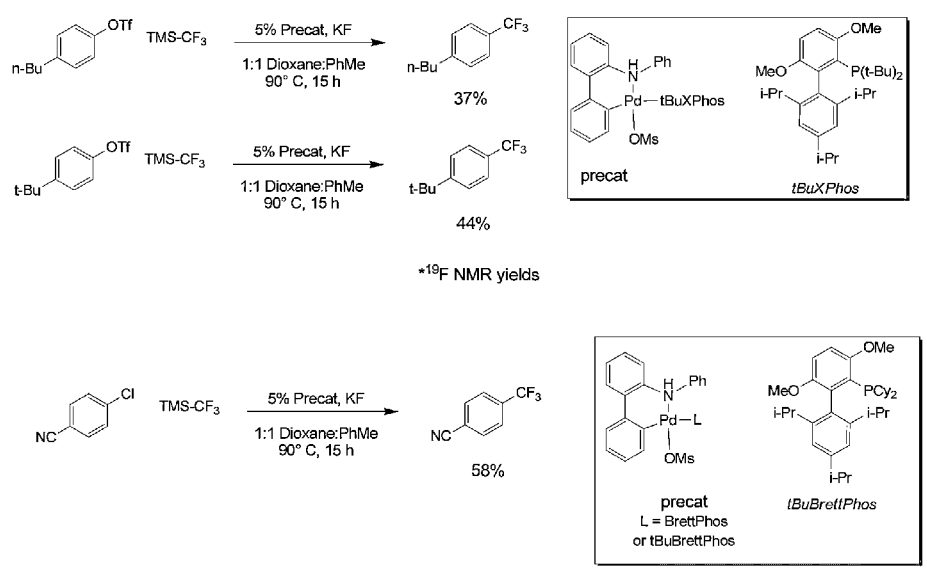
FIG. 27 depicts the trifluoromethylation of aryl triflates and an aryl chloride using precatalysts of the invention.

A test tube, equipped with a magnetic stir bar and fitted with a Teflon screw-cap, was charged with N-Phenyl-2-aminobiphenylpalladium mesylate dimer (446 mg, 0.50 mmol, 0.50 eq) and XPhos (476 mg, 1.00 mmol, 1.00 eq), followed by DCM (5 mL). The reaction was stirred at room temperature for 1 h. After completion, the reaction mixture was transferred to a scintillation vial and the solvent was removed under vacuum at room temperature. The residue was then triturated with pentane. The resulting solid was isolated via filtration and further dried under vacuum to provide the title compound as a yellow solid. See FIG. 21.

Example 12

Synthesis of N-Methyl-2-aminobiphenylpalladium Mesylate Precatalyst

N-methyl-[1,1'-biphenyl]-2-ammonium Mesylate:
A 50-mL round-bottomed flask equipped with a stir bar was charged with 2-(N-methyl)aminobiphenyl (600 mg, 3.25 mmol, 1.00 eq) and diethyl ether (25 mL). Methanesulfonic acid (212 µL, 3.25 mmol, 1.00 eq) was added dropwise and the reaction mixture was sonicated for 30 minutes and then stirred for 30 minutes. The resulting solid was filtered and further dried under vacuum to provide the title compound as a white solid. Yield: 578 mg, 61%.

N-methyl-2-aminobiphenylpalladium Mesylate Dimer

A 24-mL screw-top tube equipped with a stir bar was charged with palladium acetate (448 mg, 2.00 mmol, 1.00 eq) and a solution of N-methyl-[1,1'-biphenyl]-2-ammonium mesylate (578 mg, 2.00 mmol, 1.00 eq) in THF (10 mL). The reaction mixture was stirred at 50° C. for 15 minutes, until the solution became yellow in color. After cooling to room temperature the solvent was removed via rotary evaporation and the resulting residue was treated with diethyl ether (25 mL) to precipitate a beige solid. The resulting solid was filtered and further dried under vacuum. Yield: 530 mg, 69%.

N-Methyl-2-aminobiphenylpalladium Mesylate Precatalyst—Representative Procedure with XPhos A test tube, equipped with a magnetic stir bar and fitted with a Teflon screw-cap, was charged with N-methyl-2-aminobiphenylpalladium mesylate dimer (96 mg, 0.125 mmol, 0.50 eq) and XPhos (119 mg, 0.25 mmol, 1.00 eq), followed by DCM (5 mL). The reaction was stirred at room temperature for 1 h. After completion, the reaction mixture was transferred to a scintillation vial and the solvent was removed under vacuum at room temperature. The residue was then triturated with pentane. The resulting solid was isolated via filtration and further dried under vacuum to provide the title compound as an off-white solid.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A precatalyst of formula III:

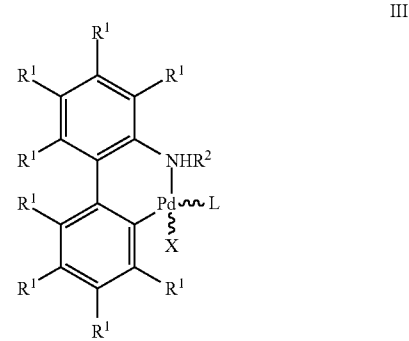

wherein, independently for each occurrence,
X is a non-coordinating anion;
R$^1$ is H, alkyl, haloalkyl, hydroxy, alkoxy, aryloxy, aryl, or halo;

L is a trialkylphosphine, triarylphosphine, dialkylarylphosphine, alkyldiarylphosphine, bis(phosphine), phosphoramide, amine, bis(amine), or N-heterocyclic carbene; and
$R^2$ is alkyl, haloalkyl or aryl.
2. The precatalyst of claim 1, wherein L is selected from the group consisting of $PPh_3$, $Ph_2P$—$CH_3$, $PhP(CH_3)_2$, $P(o\text{-tol})_3$, $PCy_3$, $P(tBu)_3$, BINAP, dppb, dppe, dppf, dppp,
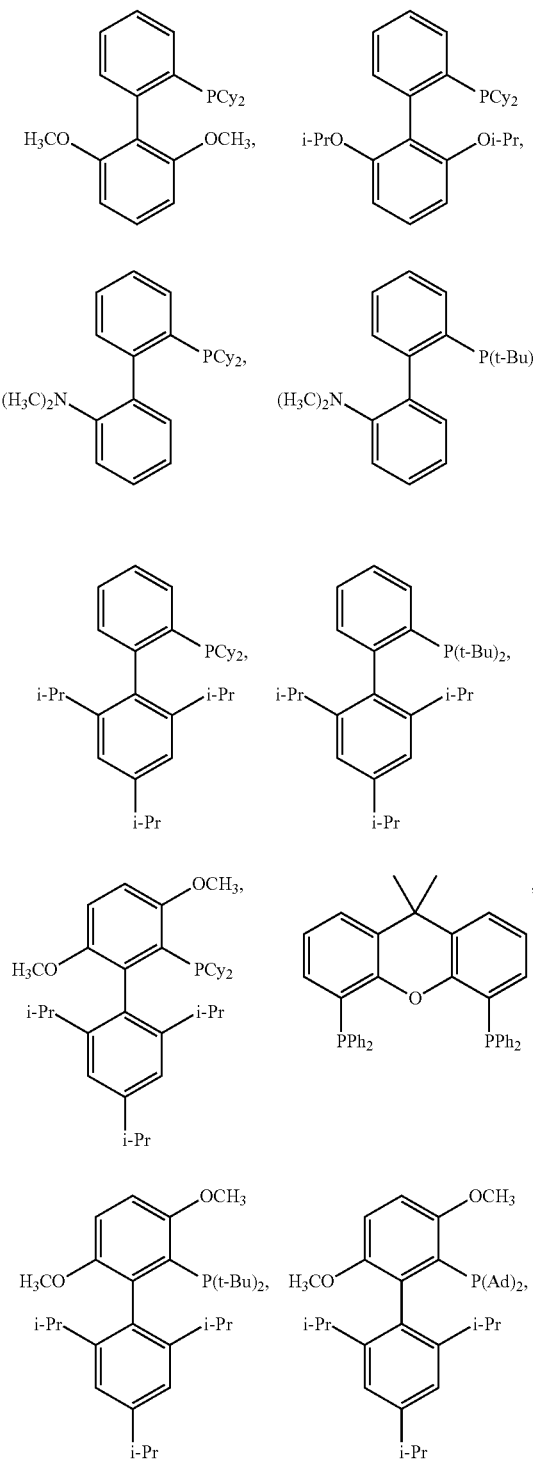
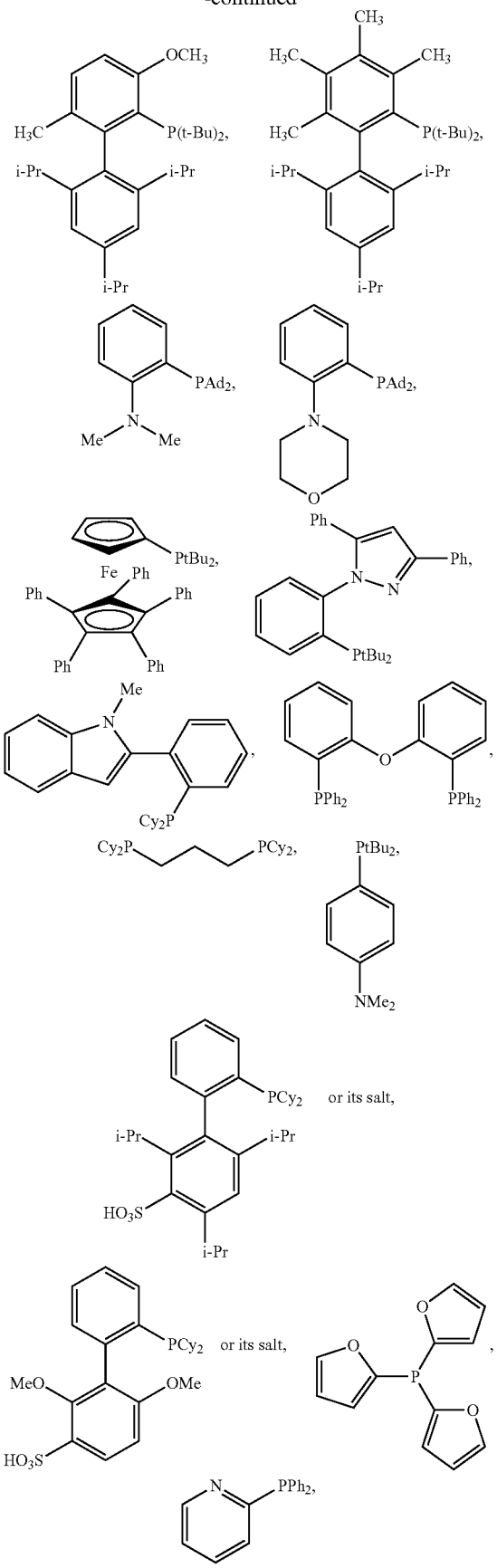

-continued

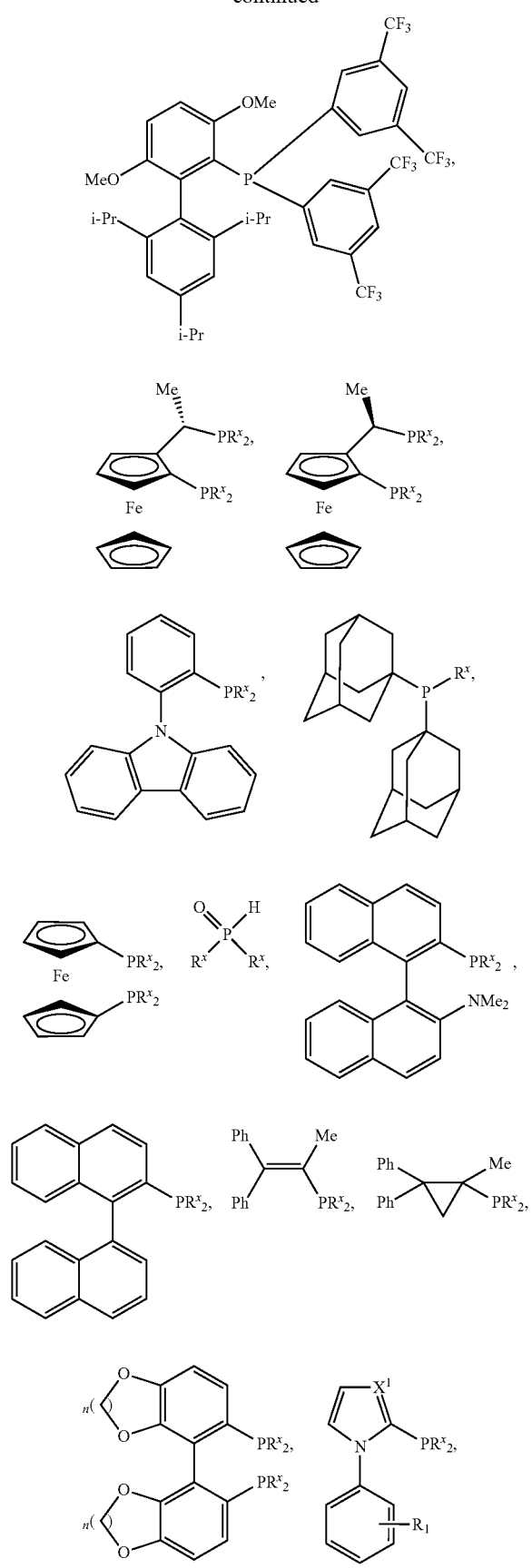

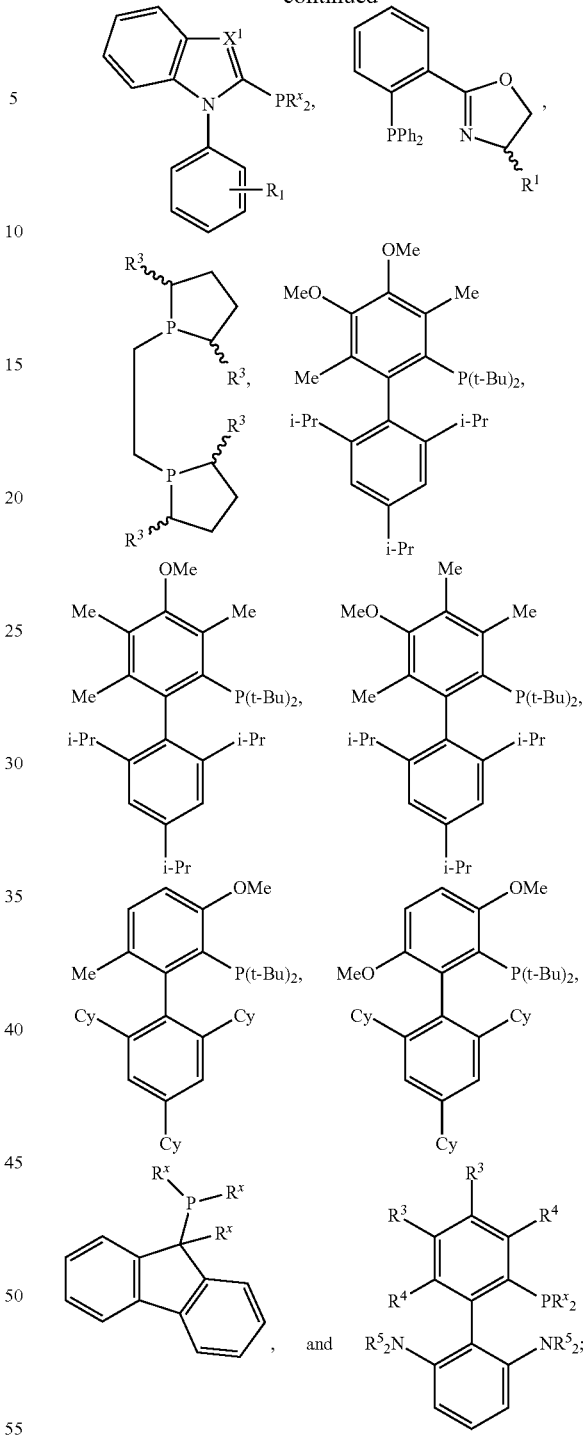

$R^x$ is alkyl, aralkyl, cycloalkyl, or aryl;
$X^1$ is CH or N;
$R^3$ is H or alkyl;
$R^4$ is H, alkoxy, or alkyl;
$R^5$ is alkyl or aryl; and
n is 1, 2, 3, or 4.

3. The precatalyst of claim 1, wherein X is selected from the group consisting of boron tetrafluoride, tetraarylborates, hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

4. The precatalyst of claim 1, wherein $R^1$ is H or alkyl.

5. The precatalyst of claim 1, wherein $R^2$, where present, is substituted or unsubstituted alkyl.

6. The precatalyst of claim 1, wherein $R^2$, where present, is substituted or unsubstituted aryl.

7. The precatalyst of claim 1, wherein the precatalyst is selected from the group consisting of:

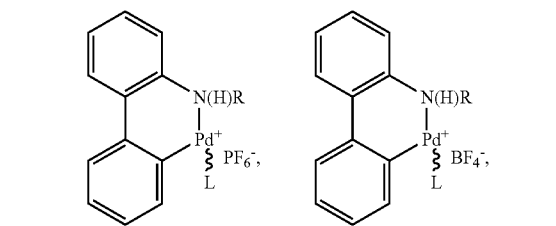

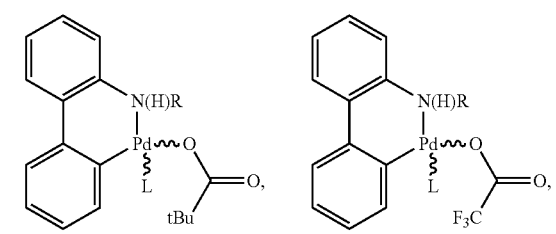

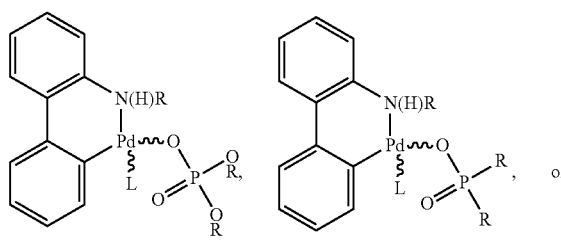

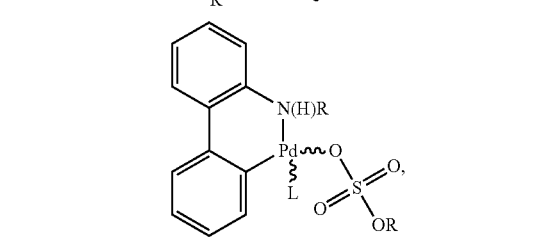

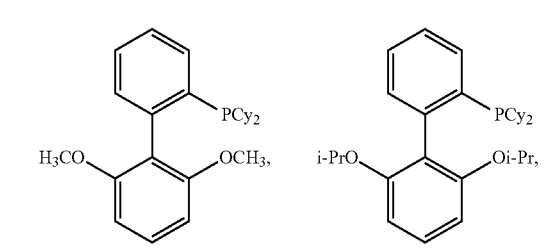

wherein R is H, alkyl, or aryl; L is selected from the group consisting of $PPh_3$, $Ph_2P-CH_3$, $PhP(CH_3)_2$, $P(o\text{-tol})_3$, $PCy_3$, $P(tBu)_3$, BINAP, dppb, dppe, dppf, dppp, -continued

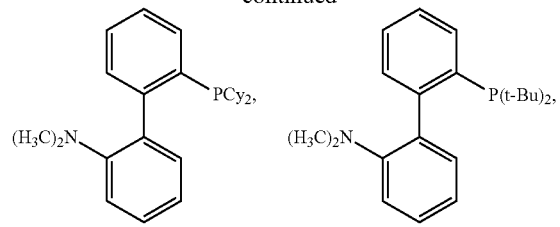

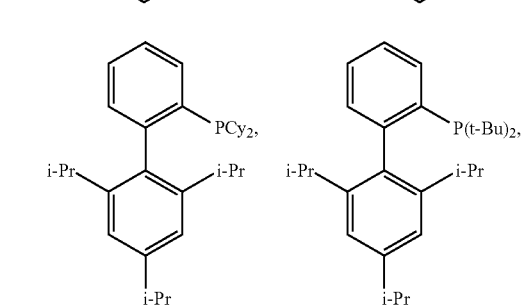

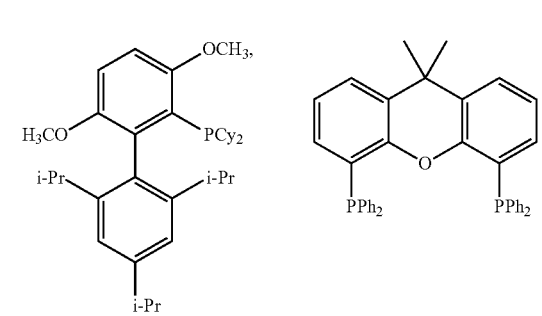

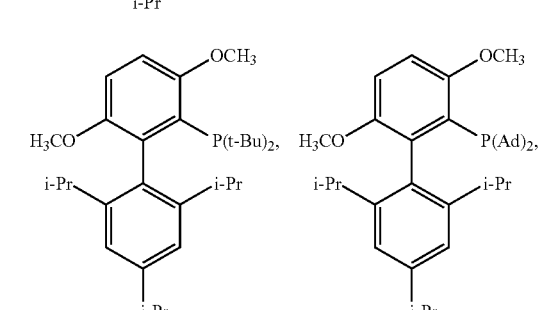

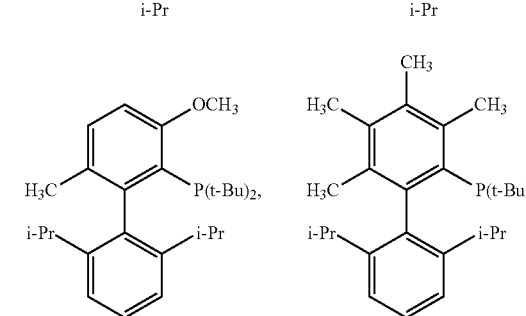

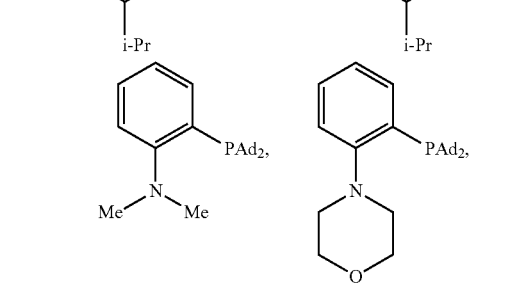

-continued
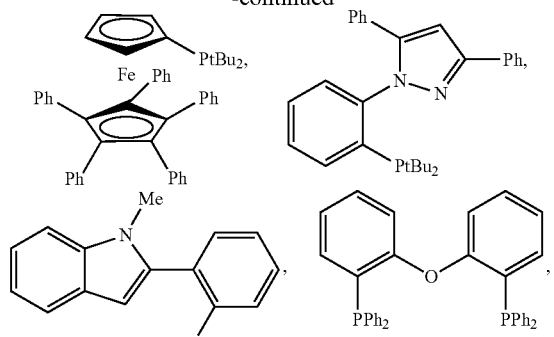
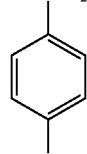
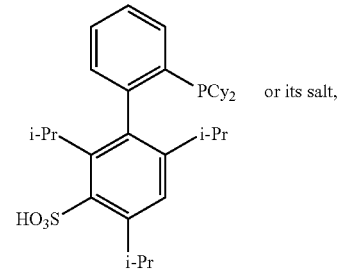
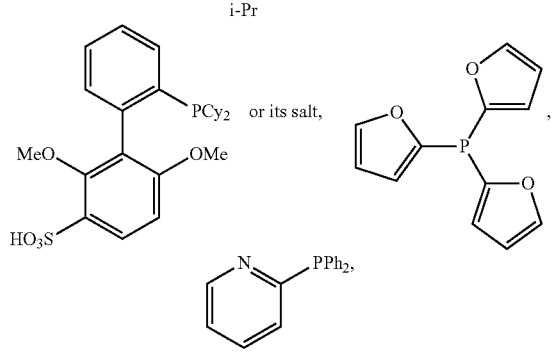
-continued
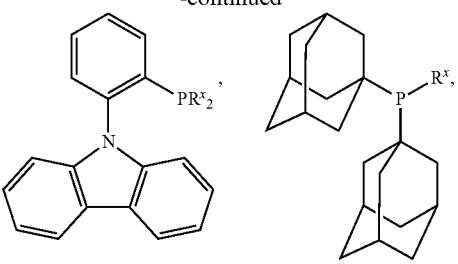
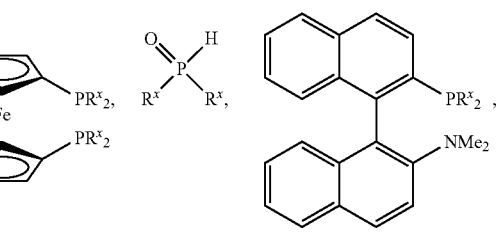
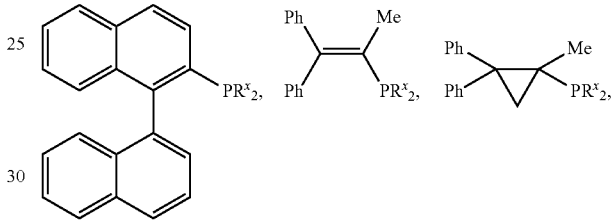
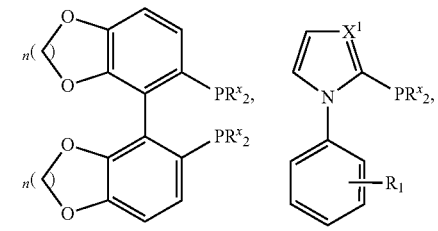
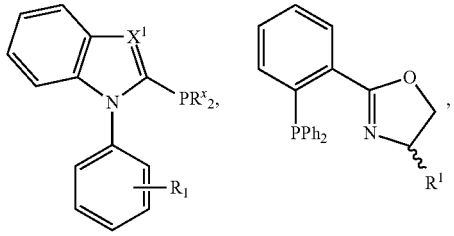
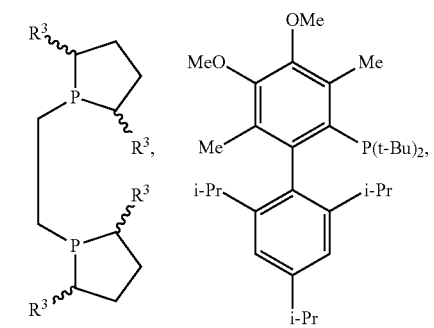

-continued

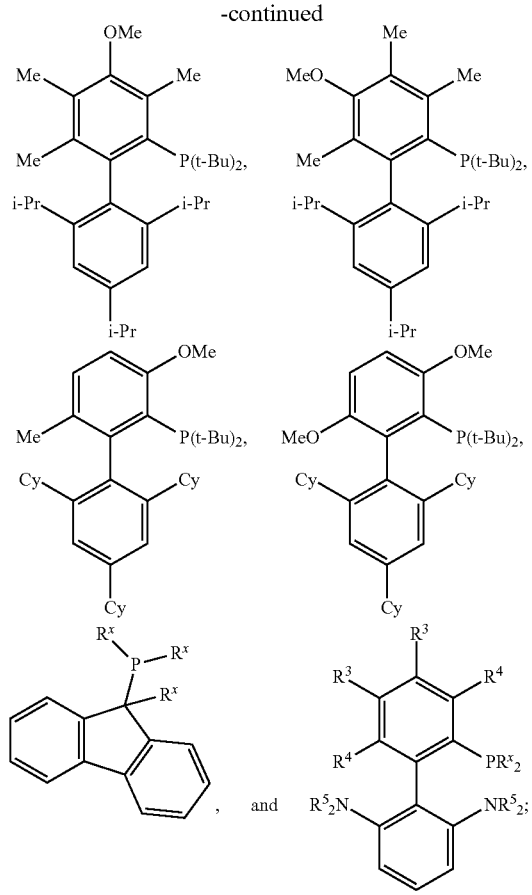

$R^x$ is alkyl, aralkyl, cycloalkyl, or aryl; $X^1$ is CH or N; $R^3$ is H or alkyl; $R^4$ is H, alkoxy, or alkyl; $R^5$ is alkyl or aryl; and n is 1, 2, 3, or 4.

8. A dimer of:

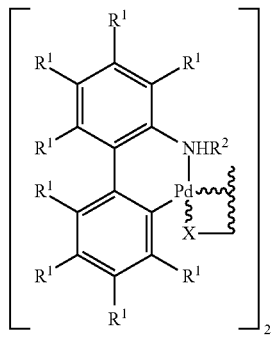

wherein, independently for each occurrence,
X is a non coordinating anion; and
$R^1$ is H, alkyl, haloalkyl, hydroxy, alkoxy, aryloxy, aryl, or halo;
$R^2$ is alkyl, haloalkyl or aryl.

9. The dimer of claim 8, wherein X is selected from the group consisting of boron tetrafluoride, tetraarylborates, hexafluoroantimonate, phosphorus tetrafluoride, phosphorus hexafluoride, alkylsulfonate, haloalkylsulfonate, arylsulfonate, perchlorate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, phosphinate, and hypochlorite.

10. The dimer of claim 8, wherein $R^1$ is H or alkyl.

11. The dimer of claim 8, wherein $R^2$, where present, is substituted or unsubstituted alkyl.

12. The dimer of claim 8, wherein $R^2$, where present, is substituted aryl or unsubstituted aryl.

\* \* \* \* \*